US006723568B1

(12) United States Patent
Liu et al.

(10) Patent No.: US 6,723,568 B1
(45) Date of Patent: Apr. 20, 2004

(54) METHOD AND APPARATUS FOR CASCADE IMPACTOR TESTING OF INHALABLE DRUG THERAPIES RECOVERY FOR CHEMICAL ANALYSIS

(75) Inventors: Benjamin Y. H. Liu, North Oaks, MN (US); Virgil A. Marple, Maple Plain, MN (US); Daryl L. Roberts, Blaine, MN (US)

(73) Assignee: MSP Corporation, Shoreview, MN (US)

( * ) Notice: Subject to any disclaimer, the term of this patent is extended or adjusted under 35 U.S.C. 154(b) by 438 days.

(21) Appl. No.: 09/679,936

(22) Filed: Oct. 5, 2000

Related U.S. Application Data

(63) Continuation-in-part of application No. 09/567,552, filed on May 5, 2000, now Pat. No. 6,453,758.
(60) Provisional application No. 60/138,742, filed on Jun. 11, 1999.

(51) Int. Cl.[7] .................................................. G01N 1/00
(52) U.S. Cl. ...................... 436/174; 73/863.22; 55/318; 55/319; 209/133
(58) Field of Search .......................... 436/174; 422/100

(56) References Cited

U.S. PATENT DOCUMENTS

| | | | |
|---|---|---|---|
| 2,538,116 A | 1/1951 | May ................................ 73/28 |
| 3,127,763 A | 4/1964 | Lippmann ........................ 73/28 |
| 3,518,815 A | 7/1970 | McFarland et al. ............. 55/241 |
| 3,693,457 A | 9/1972 | Pilat ................................ 73/28 |
| 4,133,202 A | 1/1979 | Marple ........................... 73/28 |
| 4,255,172 A | 3/1981 | Smith ............................. 55/270 |
| 4,274,846 A | 6/1981 | Smith ............................. 55/270 |
| 4,321,822 A | 3/1982 | Marple et al. .................. 73/28 |
| 4,391,151 A | 7/1983 | Nelson et al. .............. 73/863.23 |
| 4,400,982 A | 8/1983 | Bell ........................... 73/863.22 |
| 4,452,068 A | 6/1984 | Loo ................................ 73/28 |
| 4,463,595 A | 8/1984 | Yeh et al. ........................ 73/28 |
| 4,523,990 A | 6/1985 | Duyckinck ................... 209/138 |
| 4,570,494 A | 2/1986 | Dunn et al. ................. 73/863.22 |
| 4,640,140 A | 2/1987 | Burghoffer et al. ........ 73/863.22 |
| 4,725,294 A | 2/1988 | Berger .......................... 55/270 |
| 4,764,186 A | 8/1988 | Langer ........................... 55/17 |
| 4,827,779 A | 5/1989 | Marple et al. ............. 73/863.22 |
| 4,972,957 A | 11/1990 | Liu et al. ..................... 209/143 |
| 5,201,231 A | 4/1993 | Smith ....................... 73/863.22 |
| 5,343,767 A | 9/1994 | Marple et al. ............. 73/863.22 |
| 5,437,198 A | 8/1995 | John ........................... 73/863.22 |
| 5,693,895 A | 12/1997 | Baxter ....................... 73/863.22 |
| 6,101,886 A * | 8/2000 | Brenizer et al. ........... 73/863.23 |
| 6,267,016 B1 * | 7/2001 | Call et al. .................. 73/863.22 |

FOREIGN PATENT DOCUMENTS

| | | |
|---|---|---|
| DE | 2832238 A | 2/1979 |
| DE | 3110871 | 10/1982 |
| DE | 3545120 | 7/1986 |
| GB | 1354261 | 5/1974 |
| GB | 2179273 | 3/1987 |
| GB | 2351155 | 12/2000 |
| JP | 560760 A | 6/1981 |

* cited by examiner

*Primary Examiner*—Jill Warden
*Assistant Examiner*—Sam P. Siefke
(74) *Attorney, Agent, or Firm*—Westman, Champlin & Kelly, P.A.

(57) ABSTRACT

A compact cascade impactor is formed to classify particles carried in a flow through the impactor. The impactor has collection chambers that are arranged to conserve space and yet provide a large flow passageway. The collection chamber may be tear drop shaped and being nested together. The impactor includes nozzles that are used across a desired range without

15 Claims, 20 Drawing Sheets

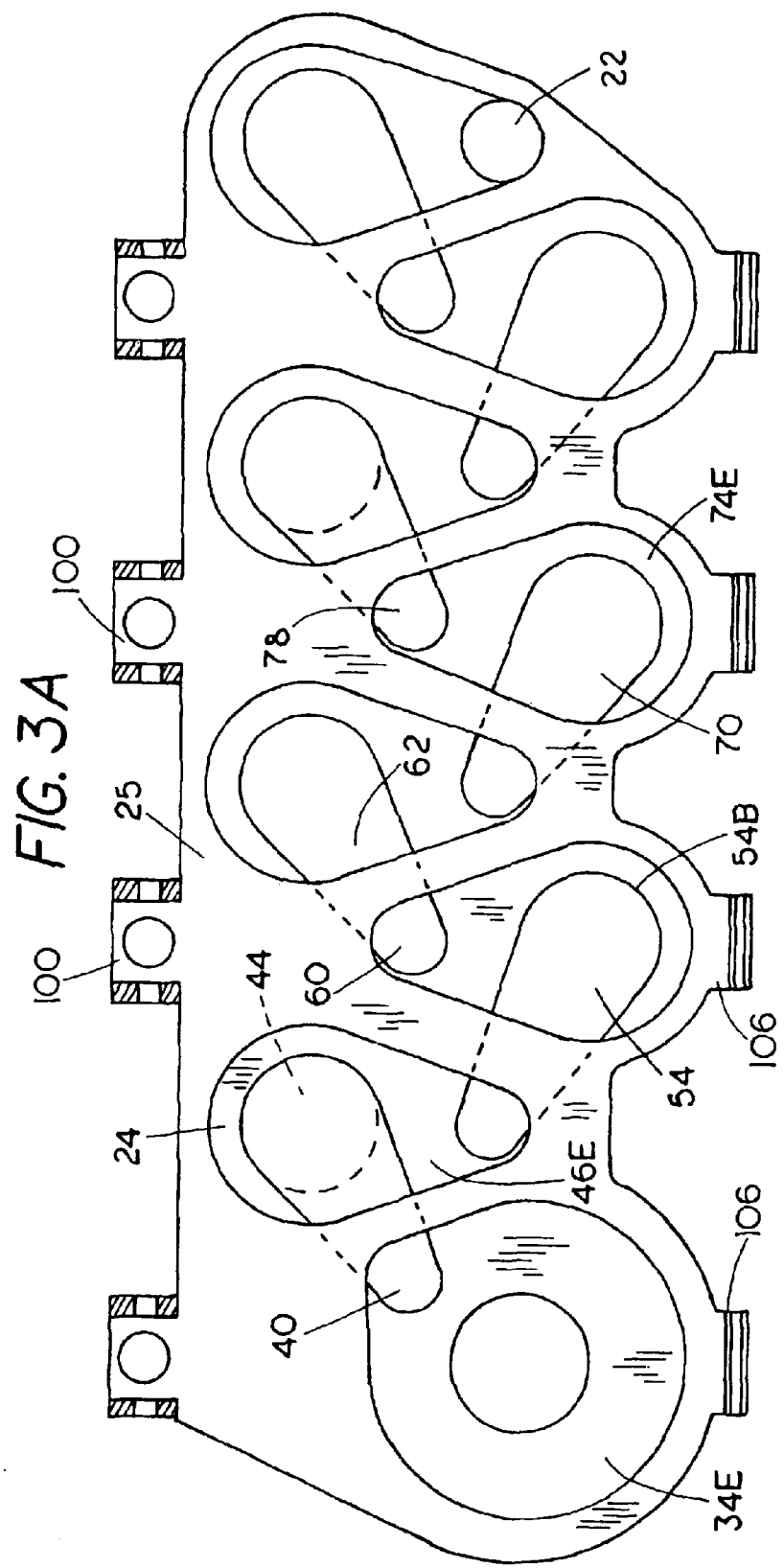

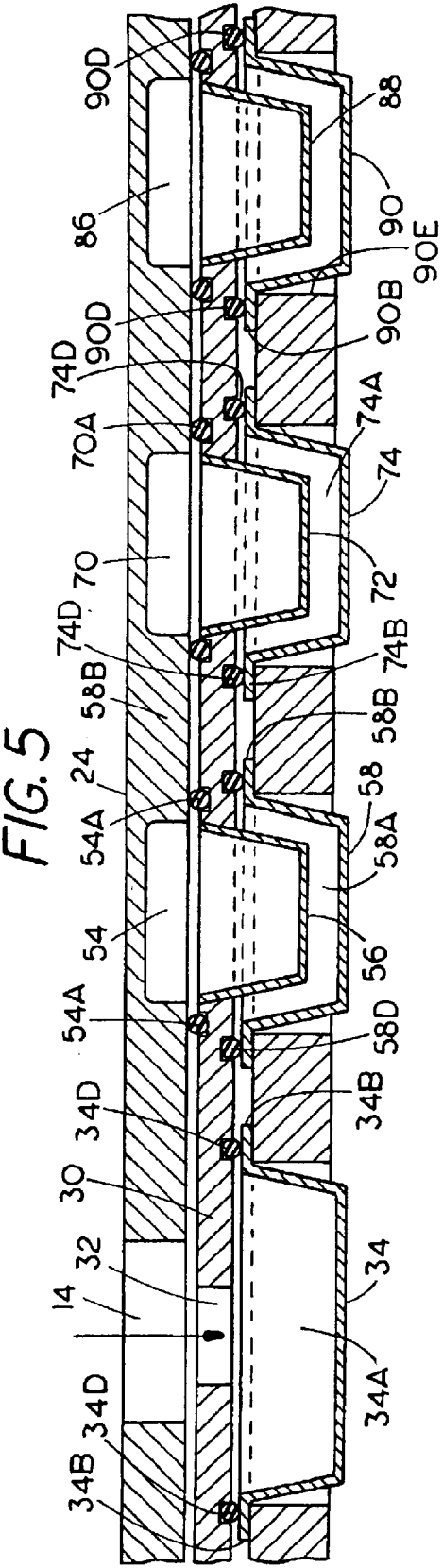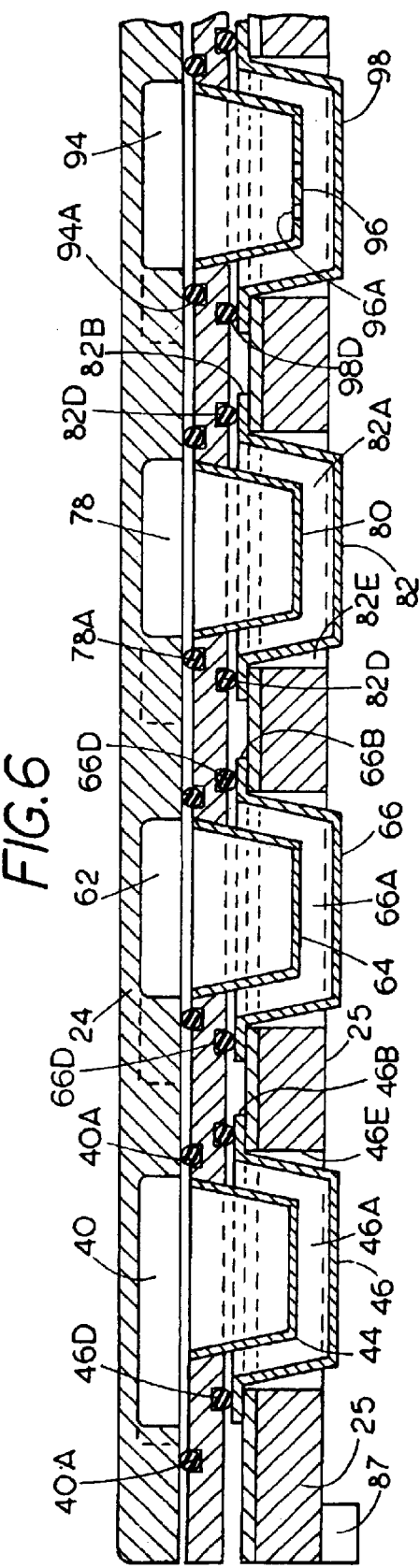

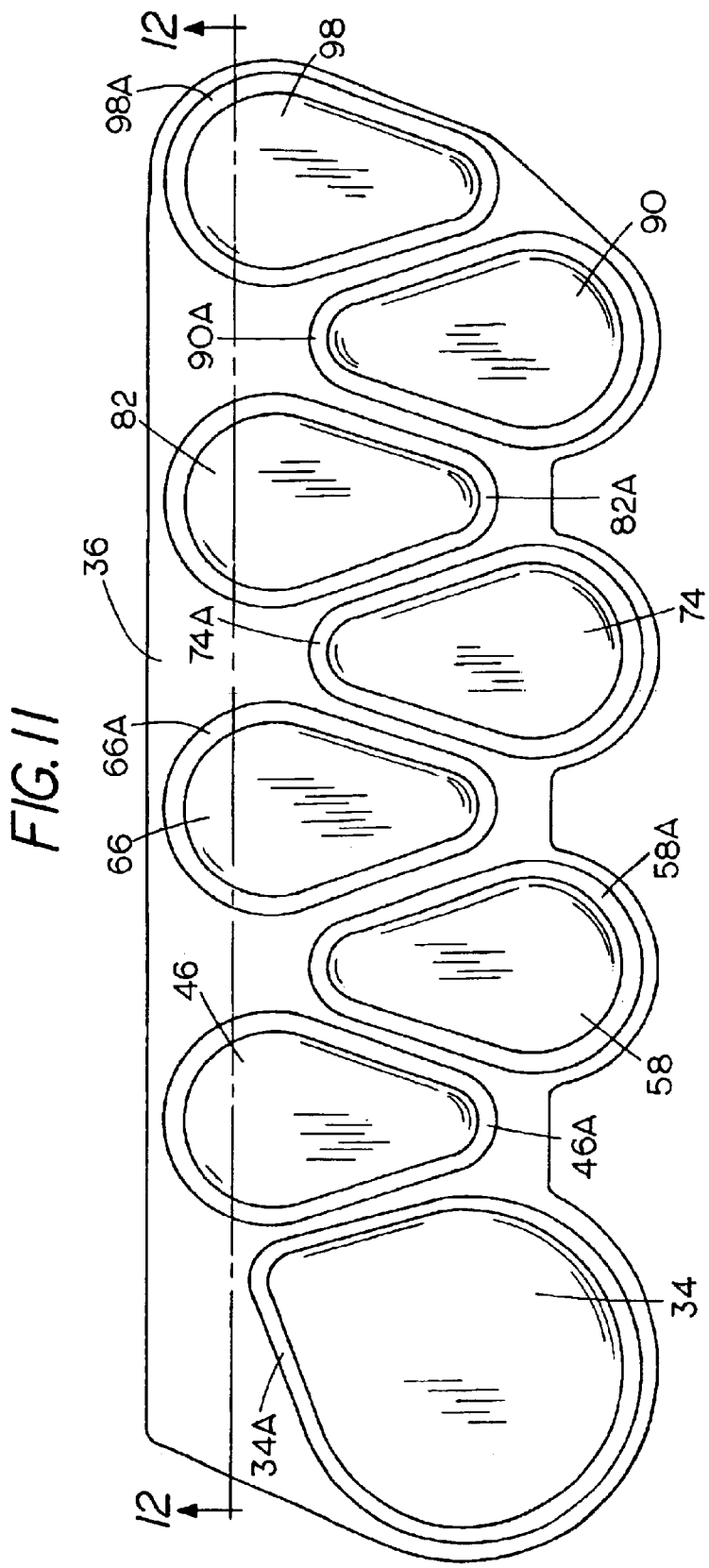

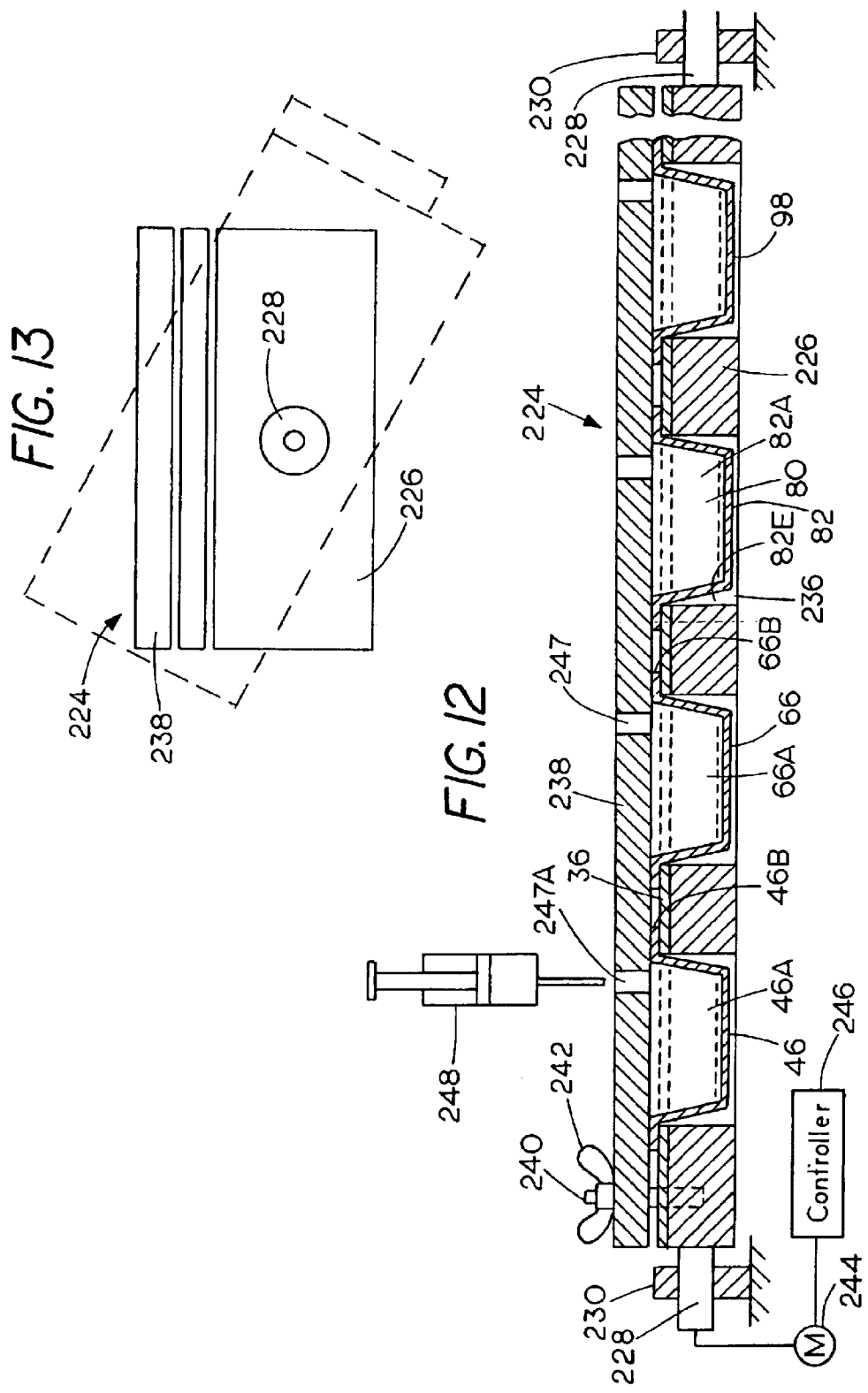

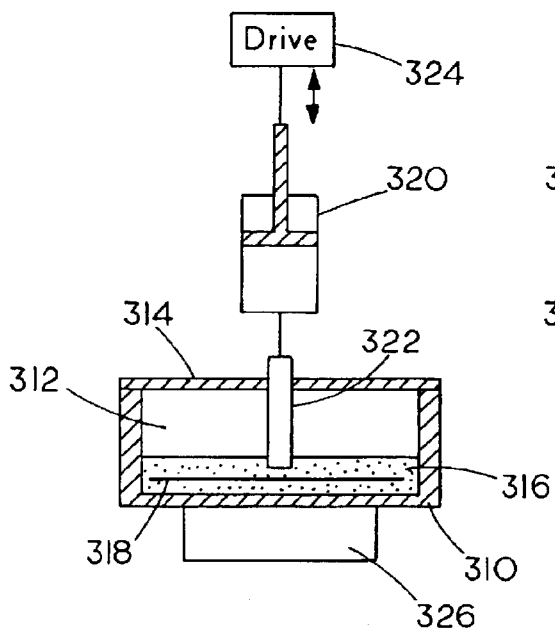
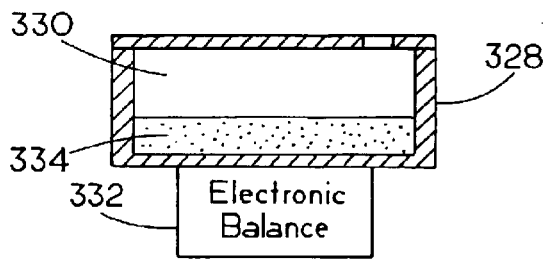
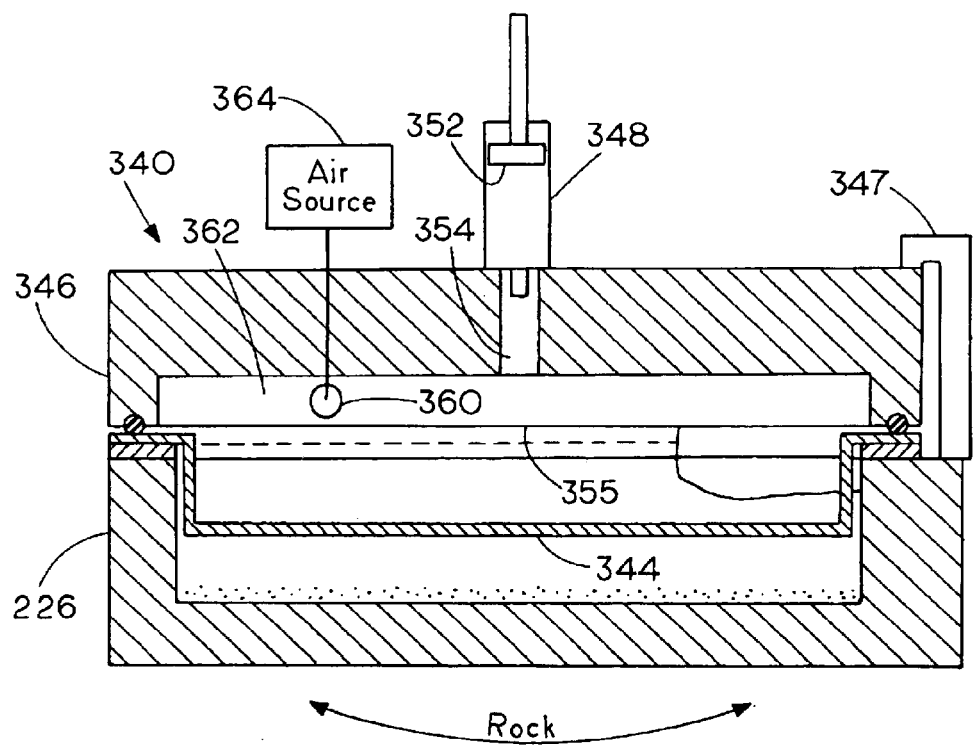

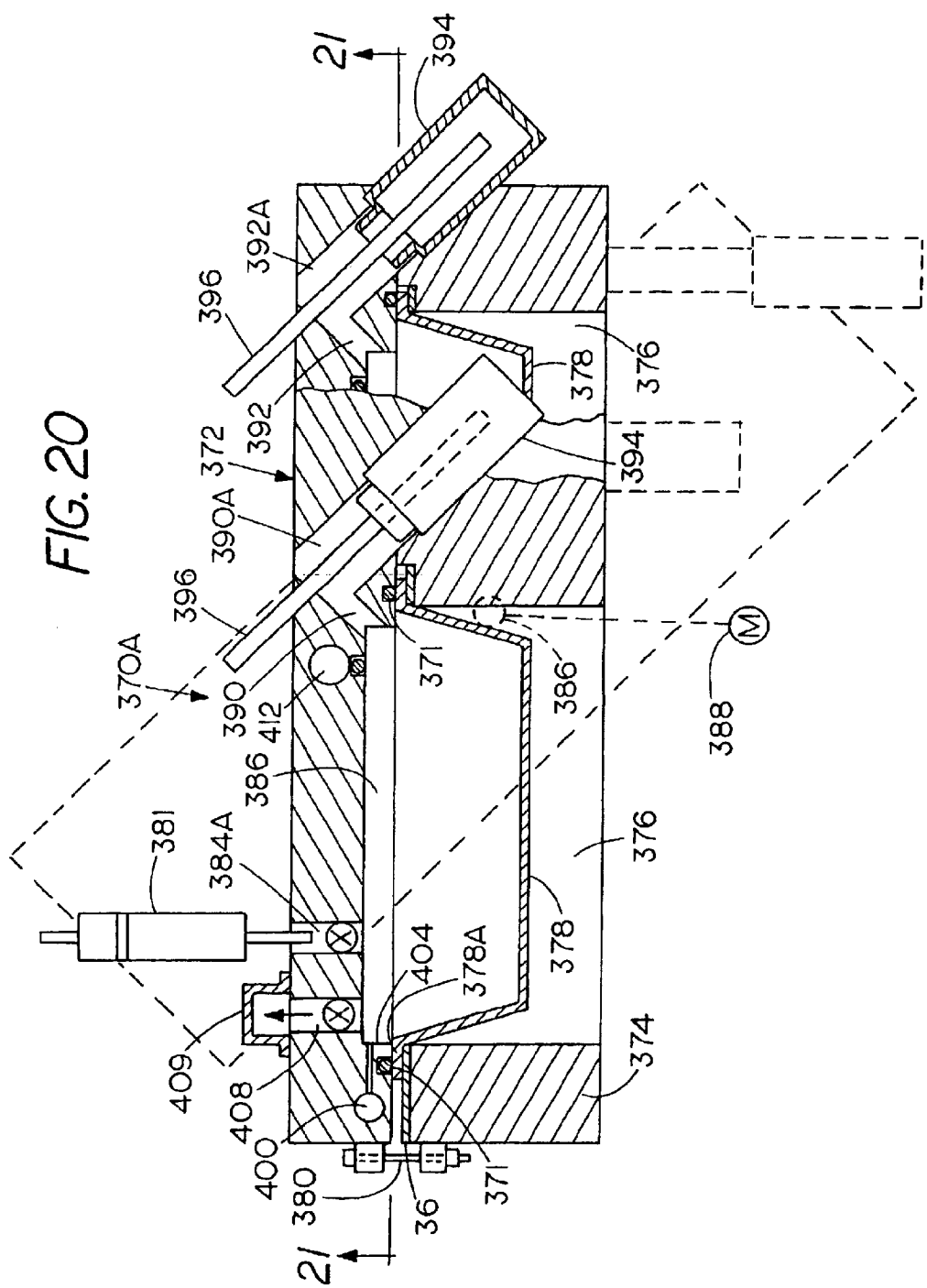

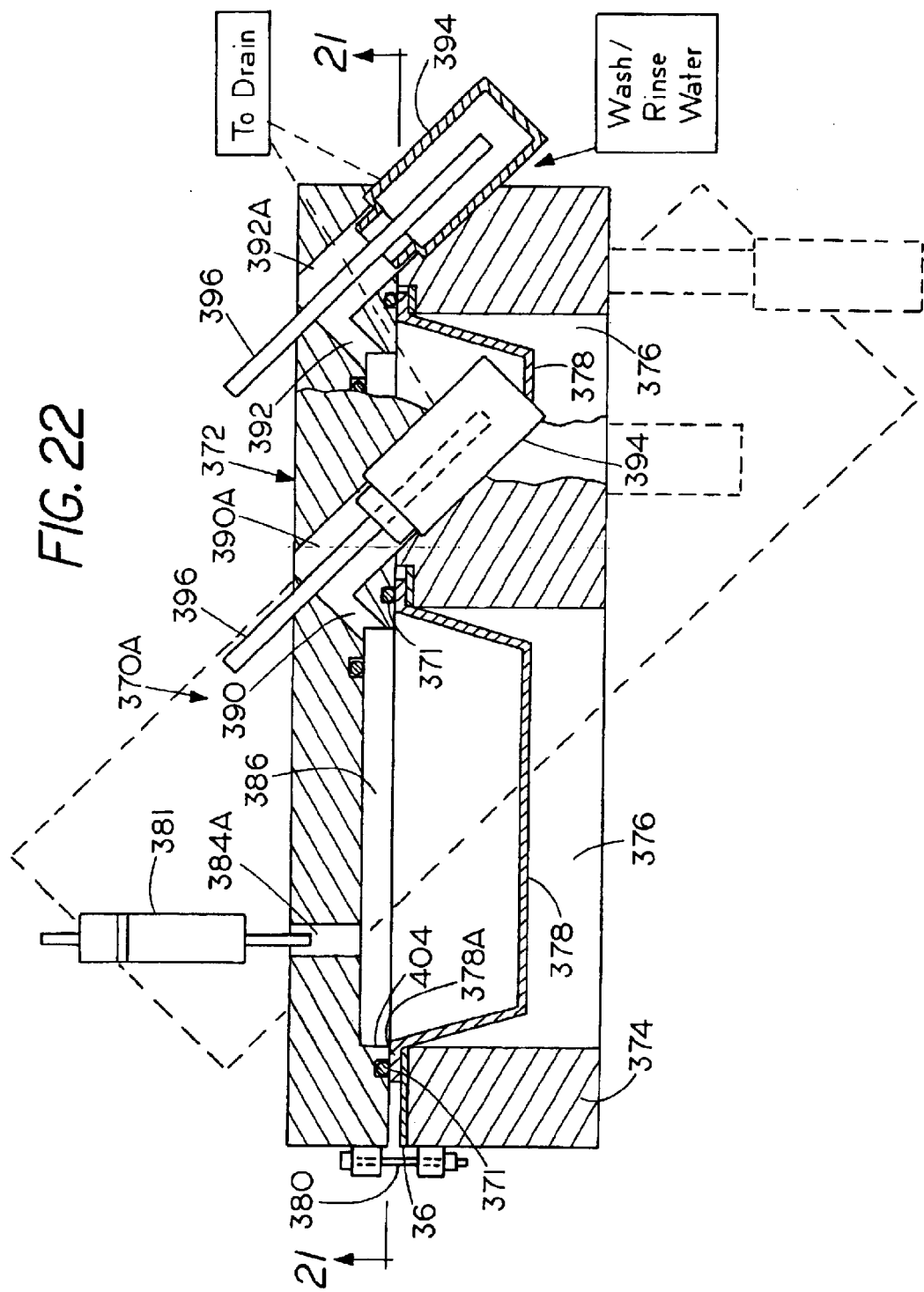

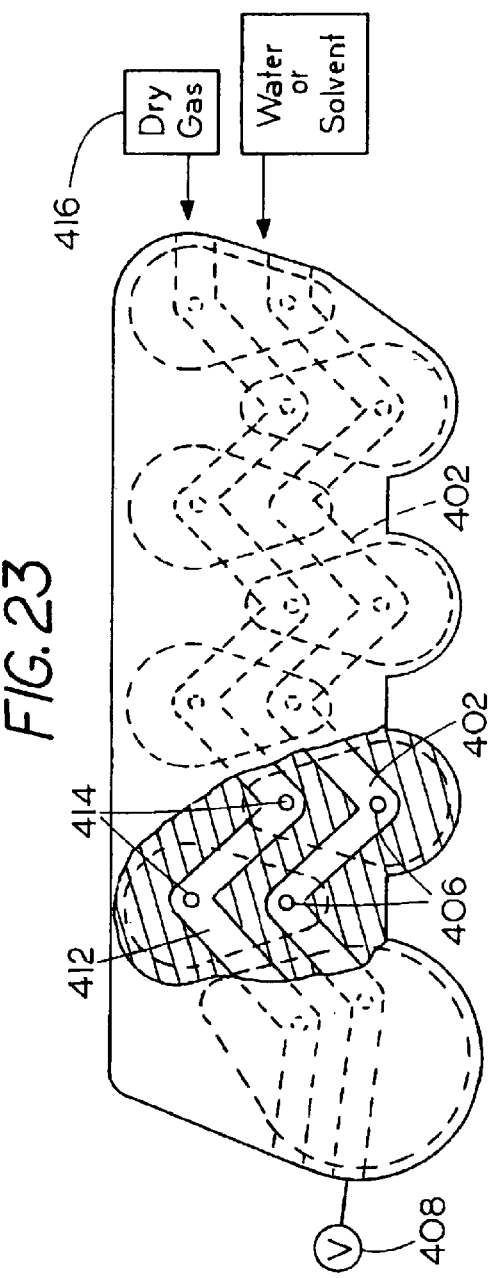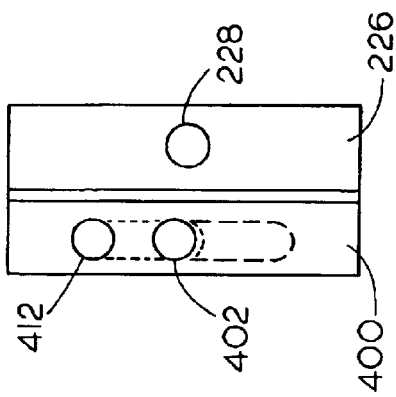

FIG. 25

| Method of Coating | Method of Solvent Addition | Method of Dissolution | Method of Sample Acquisition | Method of Waste Disposal | Method of Washing | Method of Drying |
|---|---|---|---|---|---|---|
| Manual Pipetting | Manual Pipetting | Gentle Agitation | Manual Syringe | Manual | Manual | Manual |
| Automatic Pipetting | Automatic Pipetting | Ultrasonics | Automatic Syringe | Automatic Dumping | Standard Dishwasher | Hot Air |
| Pumping in Liquid; Followed by Drying Air or Nitrogen-Enriched Air | | Mechanical Vibration | Decanting | Suction | Special Wash Station | Hot Nitrogen-Enriched Air |
| | | Direct Contact Rubbing | | | | |
| | | Recirculation | | | | |

METHOD AND APPARATUS FOR CASCADE IMPACTOR TESTING OF INHALABLE DRUG THERAPIES RECOVERY FOR CHEMICAL ANALYSIS

CROSS REFERENCE TO RELATED APPLICATION

This application is a continuation-in-part of U.S. patent application Ser. No. 09/567,552 filed May 5, 2001, now U.S. Pat. No. 6,453,758, for Efficient High Productivity Cascade Impactors which claims priority on provisional application Serial No. 60/138,742, filed Jun. 11, 1999, for COMPACT, HIGH-PRODUCTIVITY CASCADE IMPACTORS.

BACKGROUND OF THE INVENTION

The present invention relates to recovering and handling for analysis samples comprising a particle impactor. Cascade impactors are widely used for size distribution measurement of aerosols. For purpose of this invention, particles suspended in a gas are referred to as an aerosol. The gas borne particles can be a solid, a liquid, or a mixture of both. The particle size is usually between 0.002 um and 100 um.

Impactor is an aerosol-sampling device for collecting aerosol particles onto a substrate by the inertial effect of the particles. One stage of the device usually consists of a nozzle plate in close proximity to a collection plate. The nozzles in each plate which are of substantially the same size, accelerate the gas to a high velocity. The gas jets then impinge on the collection plate to cause particle collection by inertia. The particle size at which 50% of the particles are collected is known as the impactor cut-point. A cascade impactor is then several impactor stages in series, arranged so that the larger particles with large nozzle openings are collected first, followed by smaller and smaller particles.

Cascade impactors are widely used for size distribution analysis of aerosol particles. Particulate air pollutants, aerosols in the work place environment, as well as other aerosols of practical interest are usually polydiverse, with particle sizes spread over a wide range of values. Cascade impactors can be used to separate particles by size into narrower size intervals. The collected particles can then be analyzed to determine their mass size distribution or their chemical composition as a function of particle size.

An important application of the cascade impactor is the determination of size distribution of therapeutic aerosols produced by aerosol drug delivery devices such as the metered dose inhaler (MDI) and the dry-powder inhaler (DPI). Traditionally, drugs delivered in aerosol form have been used to treat asthma and other respiratory diseases. Recently, insulin delivered in aerosol form has also been found effective for the treatment of diabetes. Aerosol drug delivery is becoming increasingly important and the use of cascade impactor for testing aerosol drug delivery devices is also becoming more wide spread. For such applications, large numbers of impactor samples must be analyzed for their medicinal content. The accuracy and the efficiency with which the cascade impactor samples can be recovered and analyzed are becoming increasingly important.

Because impactor testing of drug delivery devices is very labor intensive, attempts have been made to improve the impactor design to make the process more efficient. The parent application identified above and included as part of this disclosure describes several approaches to improving the productivity of impactors. Methods to monitor the performance of the impactor are described in U.S. patent application Ser. No. 09/360,466 filed Jul. 23, 1999 to ensure consistency of operation. Productivity is limited by present particle recovery techniques.

For Recovery Of Particles

The common practice now routinely used in the laboratories to recover samples from impactors for chemical analysis is to manually place the impactor plate or cup (called substrates) on which the particles are collected in a beaker or in a funnel attached to a volumetric flask and to add solvent to dissolve the chemical compound of interest. The solution is then transferred to a sample vial by a syringe or pipette for chemical analysis by the High Performance Liquid Chromatograph (HPLC) or ultraviolet spectroscopy. The usual sample recovery process involves the following steps:

1. Disassemble the impactor and remove the sample substrates
2. Place the substrates into separate containers, such as beakers or petri dishes. For cascade impactors, as shown herein, separate containers are needed, one for each substrate.
3. A measured amount of solvent, such as methanol, is added to a substrate container. This would involve the separate steps of using a pipette to draw the required volume of the solvent, for instance, 25 ml, from the solvent reservoir, and releasing the solvent into the substrate container.
4. The substrate is allowed to remain in the container until the collected sample is dissolved into the solvent.
5. A syringe is used to withdraw the required volume of sample, for example, 1 ml, from the substrate container, and inject into a sample vial.

Steps 3, 4 and 5 usually must be repeated a total of eight to ten times, one for each of the sample substrate following sample transfer to a vial, the unused solution in the container is discarded, and the container and the impaction plate or substrate must then be cleaned for reuse.

Because of the many manual steps involved in sample recovery and impactor cleaning, a laboratory technician may take ½ to one hour to recover the samples from one impactor test run and to prepare the impactor for re-use. Because of the tedious and repetitive nature of these and related tasks, robotic impactor testing systems have been developed, for example, Novi Systems has developed a robotic system that mimics the human steps involved in sample recovery. The efficiency and speed equals the human operator, but run around the clock and are substantially error free. Robotic systems are expensive and can malfunction which shuts down the entire system.

SUMMARY OF THE INVENTION

The present invention provides for appliances to facilitate the use of cascade impactors for metered-dose and dry-powder inhaler testing including the various steps of substrate coating, particle dissolution, sample acquisition, waste solvent disposal, and washing and rinsing the substrates. It includes apparatus and procedure to make sample recovery to be more efficient, more repeatable, and with consistency.

The present invention uses individual appliances or stations for carrying out the required steps with various levels of mechanization, including manually operated, computer driven, semi-automatic and robotic appliances. The individual substrates as shown, a cup tray for example that has sample cups in it with the classified particles carried in the cup and classified according to the structure and description shown in this application. The tray is placed into a support, in the dissolution station and solvent that will dissolve the chemical or component of interest is dispensed by an automatic solvent dispenser in each cup. As will be shown this can be done either manually, semi-automatically, or utilizing a grid type syringe carrier, fully automatically. Computer controls are used for most of these steps and can be programmed to drive a syringe carrier in two mutually perpendicular directions to register the carrier with any of the cups desired according to the input program. The solvent dispenser is controlled automatically as well, to dispense the required solvent in, and if the particles are collected on substrates that are removable as small plates from the impactor, these substrates will be place into -a separate cup tray so that solvent can be added to extract the sample.

Agitation can be provided by fluid motion, that is drawing in a portion of the liquid sample and expelling it back into the cup holding it, or by ultrasonic vibration, stirring, or similar agitation techniques.

Then, a syringe can be moved into a required position for sample transfer, by drawing a portion of the sample into the syringe and moving it then to a place where it would be dispensed into a vial through a seal septum. Again, the movement of a syringe used to withdraw samples can be done on a computer controlled three axis handler.

To accurately measure the amount of solvent dispensed, a calibration cell is used for weighing by electronic balance after the particles of interest have been dissolved.

The apparatus shown can also be used for manual manipulation, rocking, decanting and the like. Different types of supports, cups and other apparatus can also be used.

In the process, the cups or the substrates for collecting particles can be treated with a coating that is "anti-bounce" coating as an optional step. Further the particular types of washing stations and holders can be varied as desired.

The present invention thus discloses methods and apparatuses for working with cascade impactors as they are used for testing metered-dose and dry-powder inhalers for recovering samples that are provided from existing cascade impactors, in an efficient and low cost manner.

BRIEF DESCRIPTION OF THE DRAWINGS

FIG. 5 is a sectional view taken as on line 5—5 in FIGS. 2 and 3;

FIG. 6 is a sectional view taken as on line 6—6 in FIG. 2;

FIG. 11 is a top plan view of a tray holding cups with samples in them, which is removed from the impactor in the first form of the invention shown in FIGS. 1 through 7;

FIG. 12 is a sectional view of a typical sample recovery station made according to the present invention showing a syringe that is used for injecting a solvent into each of the cups, and providing for mounting all of the cups from a single sample run of the impactor of FIG. 1 in a unitary assembly;

FIG. 13 is an end view schematically shown of the device of FIG. 12;

FIG. 17 is a schematic representation of sample extraction with a pumping action for stirring the substrate;

FIG. 18 is a schematic cross sectional view of a calibration cell in which solvent can be placed both before adding to a cup, and afterwards, for calibrating the system;

FIG. 19 is a schematic representation in cross section of a station in which a sample recovery cup or impactor plate can be coated with an anti-bounce material;

FIG. 20 is a schematic cross sectional view of a dissolution and sample acquisition typical wash station that can be used with the present invention, that also can be used as a wash station after the samples have been recovered.

FIG. 22 is a view of a manual station similar to FIG. 20;

FIG. 23 is a plan view of a manual, wash and dry manifold used with a tray full of cups;

FIG. 24 is an end view of FIG. 23; and

FIG. 25 is a chart showing various combinations of steps in sample handling.

DETAILED DESCRIPTION OF THE ILLUSTRATIVE EMBODIMENTS

Figure 1:
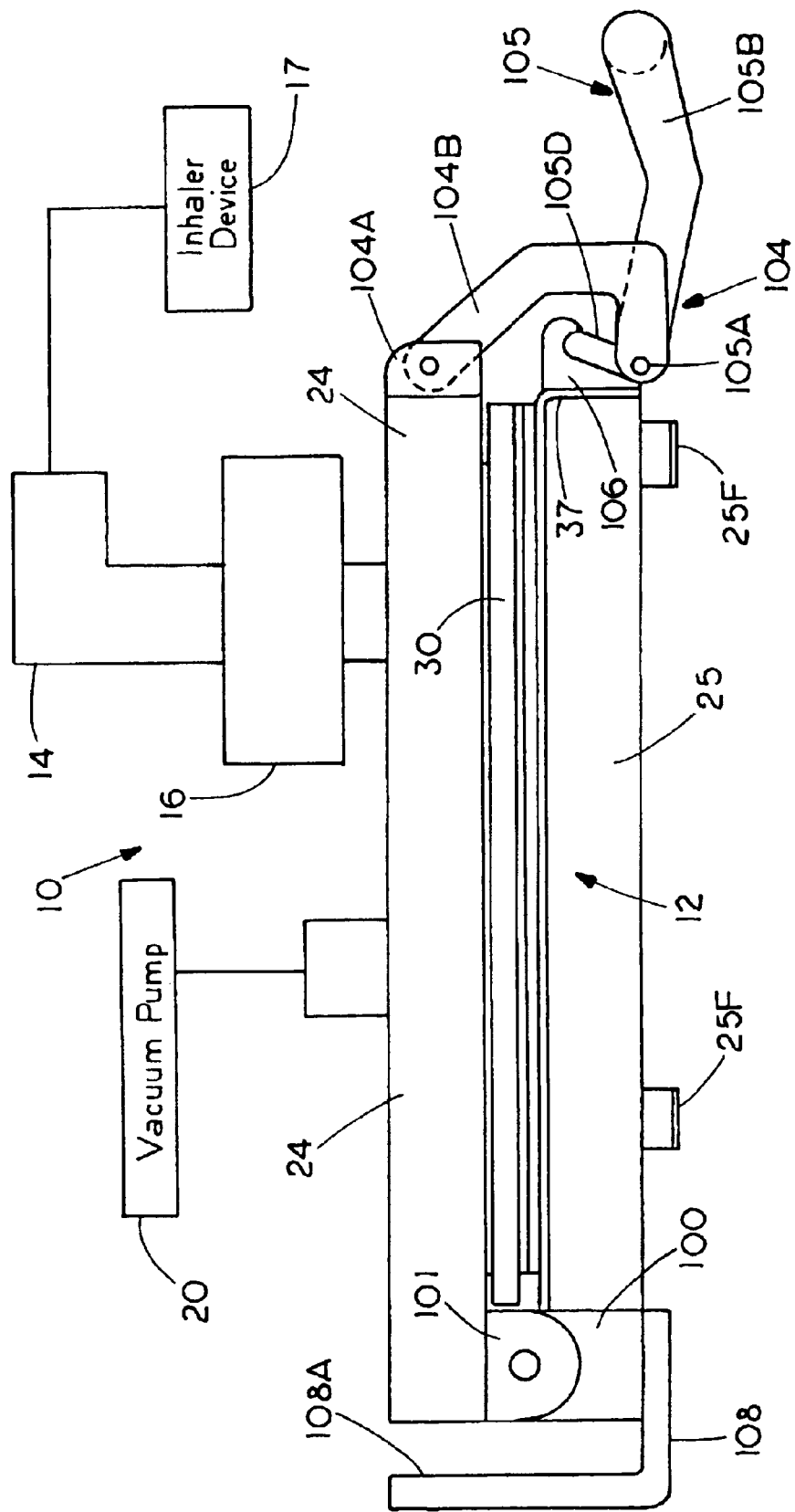
FIG. 1 is a side view of an impactor made according to the present invention.

A first form of the invention illustrated in FIGS. 1 through 6 comprises an impactor assembly 10, which has a housing assembly 12, with an aerosol inlet 14 of standard size described in USP 24, Section 601. The inlet can be a standard USP type inlet tube. A pre-separator 16 is illustrated on the inlet in FIG. 1, and it is used to separate out large particles with a standard type impactor arrangement.

The aerosol that is passed through the impactor 10 is an aerosol generated by a hand-held inhaler 17 or other device that may be a liquid or dry powder drug inhaler, such as those used to control asthma and similar problems. The amount of flow from each charge is small, so the internal volume of the impactor 10 must be kept low. For testing dry powder inhalers, accepted methods call for the total volume of sampled air to be between 2 liters and 4 liters. Therefore, the internal volume of the impactor must be low to achieve proper particle sizing. The internal volume or dead volume is preferably 1 to 2.5 liters. Small dead volume is important for achieving steady state flow during a typical breath volume of 2 to 4 liters. Steady state flow is achieved in about 0.2 seconds. The entire test is completed in 2 to 4 seconds. The flow rate through the impactor will be generated in a selected manner, for example by providing a vacuum pump such as that shown at 20 on an exhaust or flow outlet opening 22 from the impactor housing 12.

The impactor 10 of the first form of the invention is made to be compact so that it is easily used, portable and does not take up much space, and can be operated in a normal manner. The impactor 10 of the first form of the invention has a lid or cover 24 that is sufficiently thick to include flow passageways on the underside. The lid or cover 24 has the inlet 14 at one end thereof. The lid or cover 24 is hinged along one edge to a base frame 25 that has a number of egg shaped or tear drop shaped openings that receive and support tear drop shaped impactor particle collection chambers or cups as will be shown.

As shown in FIGS. 3, 4, 5 and 6 a seal plate 30 is positioned just below the cover or lid 24 and as will be explained, has seals on both sides to seal passageways on the underside of the cover and, on the opposite or bottom side of the seal plate, to seal around lips of each of the impaction chambers or cups to define sealed passageways for forming the flow path. The collection chambers or cups will be individually numbered in this description. The first cup at the inlet is shown at 34, and is larger than the rest. Inlet opening 14 in cover 25 opens through an inlet opening 32 that sealingly opens through the seal plate 30 and cover or lid 24 into a chamber or passageway 34A defined by the first impaction stage cup 34. Cup 34 fits through an opening in a cup retainer tray or frame 36. The cup 34 has a peripheral flange 34B that rests on the tray or frame 36. The cup also fits in an opening 34E in the frame 25. The tray or frame 36 is supported on the top of the base 25.

The impaction cups are tear drop shaped as shown. The bottom wall at the large end 34E of the first stage cup (and all cups) forms the impactor surface and underlies the inlet opening 32. The flange 34B of the cup 34 is sealed with a seal 34D on the seal plate and extends transversely of the impactor to a vertical passageway 38 that opens through the seal plate 30 to interface or crossover passage 40 formed on the underside of the cover 24.

Figure 3:
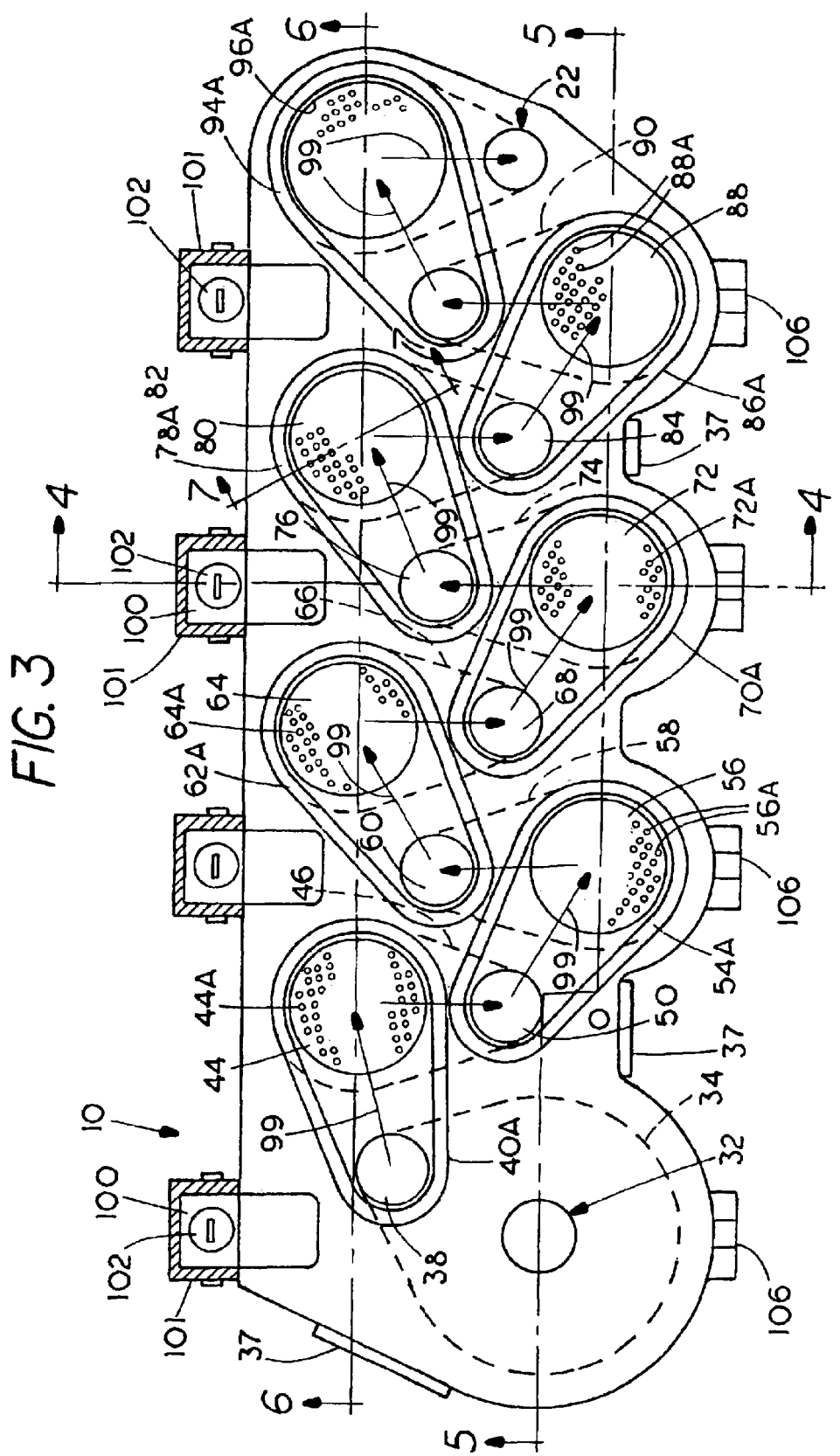
FIG. 3 is a top plan view thereof with the top cover removed.

FIG. 3A is a bottom view of the base, with the cups and seal plate removed, so the interstage passages on the underside of the cover 24 can be seen. The openings in the cups on the base frame 25 are designated with the cup number followed by the letter "E". The seals on the peripheral flanges of the cups follow the shape of the cup openings in frame 25 shown in FIG. 3A, and as shown in dotted lines in FIG. 3.

The crossover or interstage passageway 40 leads to a nozzle passageway or opening in seal plate 30 (FIGS. 3 and 6) having a nozzle 44 that has openings 44A of desired size, and desired number. Particles will discharge into a second stage impactor surface of a cup 46 held in an opening 46E of base 25, under nozzle 44. The tear drop shaped cup 46 has a wide end under the nozzle 44 and a narrow opposite end. The cup 46 has a flange 46B for support and defines a passageway 46A. The small end of the cup 46 aligns with a passageway or port 50 through the seal plate and opens to a tear drop shaped passageway 54 in the cover 24.

The large end 54B of passageway 54 overlies an opening in seal plate 30 which holds a nozzle 56 that has openings 56A. Nozzle 56 overlies a tear drop shaped cup 58. The openings 56A are smaller and greater in number than the openings 44A, and the nozzle openings decrease in size in the impactor stages to the outlet. The third stage impactor cup 58 has a flange 58B and forms a passageway 58A (see FIGS. 3, 3A and 5) that opens to a vertical passageway 60 in seal plate 30 and to a passageway 62 in the cover 24. That in turn connects to a nozzle 64 that discharges into a cup 66.

A passageway 64A that extends laterally opens through seal plate 30 and connects to a tear drop shaped passageway 70 in the cover 24 which directs flow through a nozzle 72.

A cup 74 with a flange 74B provides a fifth stage impactor and underlies the nozzle 72 and receives particles discharged through the nozzle 72. The cup 74 also forms a passageway 74A leading to an opening 76 and to a passageway 78 in the underside of cover 24. Cup 74 fits in opening 74E in the base, shown in FIG. 3A. Cups 66 and 74 are also shown in FIG. 1, where the impactor cover and seal plate are broken away.

The crossover passageway 78 carries flow to a nozzle 80, with openings 80A, so flow goes downwardly into an underlying sixth stage impactor cup 82 supported with a flange 82B. The cup 82 forms an impaction plate and provides a passageway 82A. Passageway 82A leads to an opening 84 and then to a passageway 86 in the underside of cover 24.

The passageway 86 leads to a nozzle 88 that has openings 88A that open to an underlying cup 90 forming a seventh impaction stage. The cup 90 is supported on a flange 90B and forms a passageway 90A that leads through an opening 92 to a passageway 94 in the cover 24.

The passageway 94 opens to a final stage micro orifice filter nozzle 96. The micro orifice filter nozzle 96 discharges the flow into an underlying cup 98 with a support flange 98B that opens to the fluid flow outlet passage 22 from the impactor.

The seal plate 30, as shown, and as was explained, has "O" ring type seals for the passageways in the cover and to seal on the impactor cup flanges.

The passageways in the cover that connect between nozzles are all sealed with tear drop shaped O-ring seals. Passageways 40, 54, 62, 70, 78, 86, and. 94 are sealed with seals 40A, 54A, 62A, 70A, 78A, 86A, and 94A, respectively. The flanges on the impactor cups are also sealed with tear drop shaped seals. In addition to the seal 34D, the cups 46, 58, 66, 74, 82, 90, and 98, are sealed with seals 46D, 58D, 66D, 74D, 82D, 90D, and 98D, respectively.

The cover 24 is hinged to the base with a pin that is spring loaded to permit some desired resilient movement perpendicular to the seal plate to provide compression of the seals on the seal plate 30. The hinging between the cover 24 and the base 25 may be made so that as compression of the seals on the seal plate 30 occurs, the surfaces that engage the seal plate, namely the flanges on the impactor cups and the under surface of the cover, remain parallel.

Figure 2:
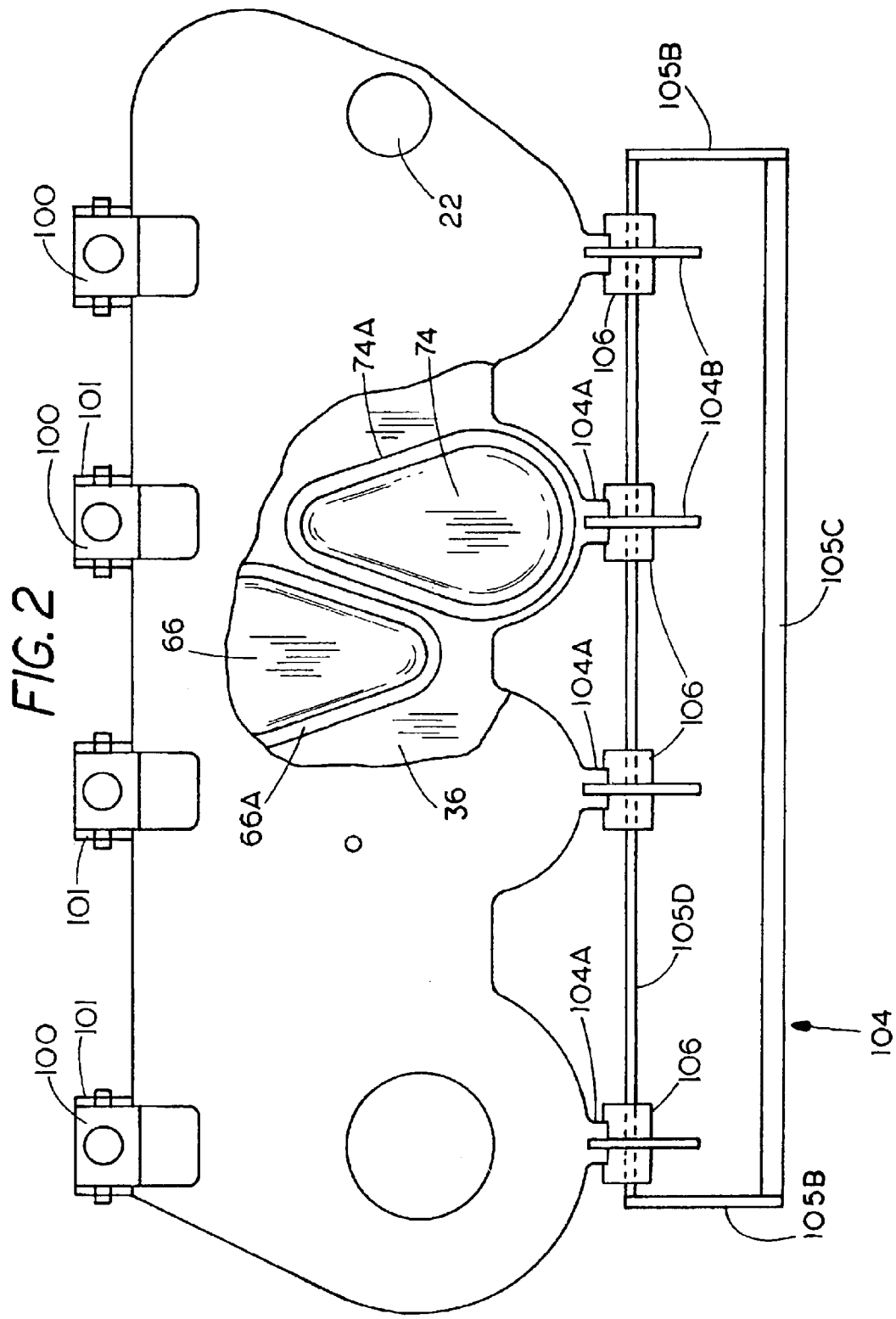
FIG. 2 is a top plan view thereof with parts broken away.
Figure 4:
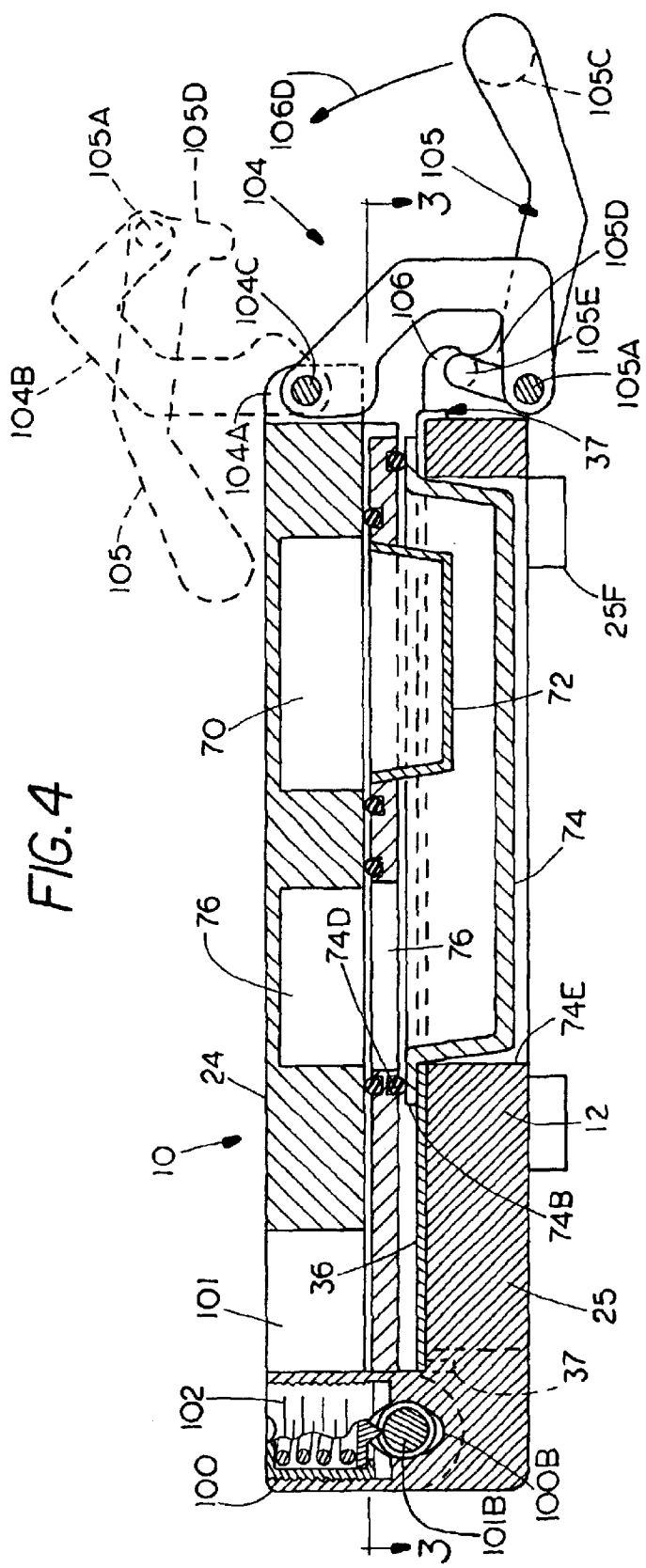
FIG. 4 is a sectional view taken as on line 4—4 in FIGS. 2 and 3.

As shown schematically in FIGS. 1, 2 and 4, the base 25 has a plurality of upright hinge posts 100, that are spaced along the hinging edge of the base and cover, and the cover has sets of flanges 101, that fit on the opposite sides of the respective posts 100. The flanges 101 carry a pivot pin 101B that passes through a slot 100B in each of the upright posts 100. The pin is urged downwardly with a spring loaded, threaded plunger 102 that is threaded into a bore in the respective hinge posts. The spring loaded plunger is a purchased unit that has an internal spring and a centering point at the lower end thereof that rides in a groove in the pin 101A. This will keep the pin centered and held in the hinge post 100.

In order to have an adequate compression load on the seals, a cam type latch assembly 104 is utilized, and is shown in FIGS. 2 and 4, primarily. The latch assembly 104 is supported on ears 104A that are on the cover member, through first pivot arms 104B. The hinge members or ears 104A have pins 104C that permit the arms 104B to pivot upwardly and downwardly. The solid line position in FIG. 4 shows the cam latch assembly 104 in locked position, and the dotted line position shows it released.

A latch handle assembly 105 is pivoted to the arms, with pins 105A. The handle assembly 105 comprises a pair of end arm members 105B, 105B as shown in FIG. 2, connected with a handle rail 105C that comprises a hand grip, and the handle arms 105B are also joined with a latch bar 105D.

The base 25 carries a plurality of latch hooks 106, that receive nose portions 10SE of the latch bar 105D. The pivots are arranged for an over center latch action. The latch is released by pulling up on handle 105C in direction of arrow 108D.

As shown in FIG. 1, the base 25 has support feet 25F, and at the hinge end, a bracket 108 is provided that can be fixed to the hinge bosses 100. The bracket 108 has an upright leg 108A that is rigidly attached to the lower portion of the leg, and when the unit is turned up on edge, the bracket 108A will support the impactor assembly 10 with the hinge edge downwardly, letting it stand in an upright position with the handle extended upwardly.

The bottoms of the cups are supported so they clear the supporting surface. This means that when the cover is opened, after the test has been run, tray 36 can be lifted out of the bottom frame, manually or with a fixture. When the tray is lifted all of the impactor cups are removed as a unit. The cups may be placed either in a separate container and sealed, or as disclosed simultaneously processed for recovering and analyzing the particles in each impactor cup.

The ability to lift all of the cups at once makes manual or mechanically assisted operation easier, because the cup tray can be installed in racks and moved as a unit. The cup tray has locating flanges 37 that act as feet when the tray is removed. The locator flanges 37 lap over the edges of the base to keep the tray 36 in place.

The cups also have outwardly tapered side walls so they can be nested and stacked for storage.

The flow paths are shown essentially in FIG. 3, with arrows 99. The flow path is from the inlet to the outlet. The path is divided into segments, forming impaction stages, by the nozzles.

The nozzles and the orifice sizes are selected to provide at least 5 cut points at all desired flow ranges that are between 0.4 $\mu$m and 6.0 $\mu$m. In addition, one stage should provide particles between 5 $\mu$m and 10 $\mu$m. A pressure drop across the impactor of less than 100 inches of water at the maximum flow rate is desired.

Figure 7:
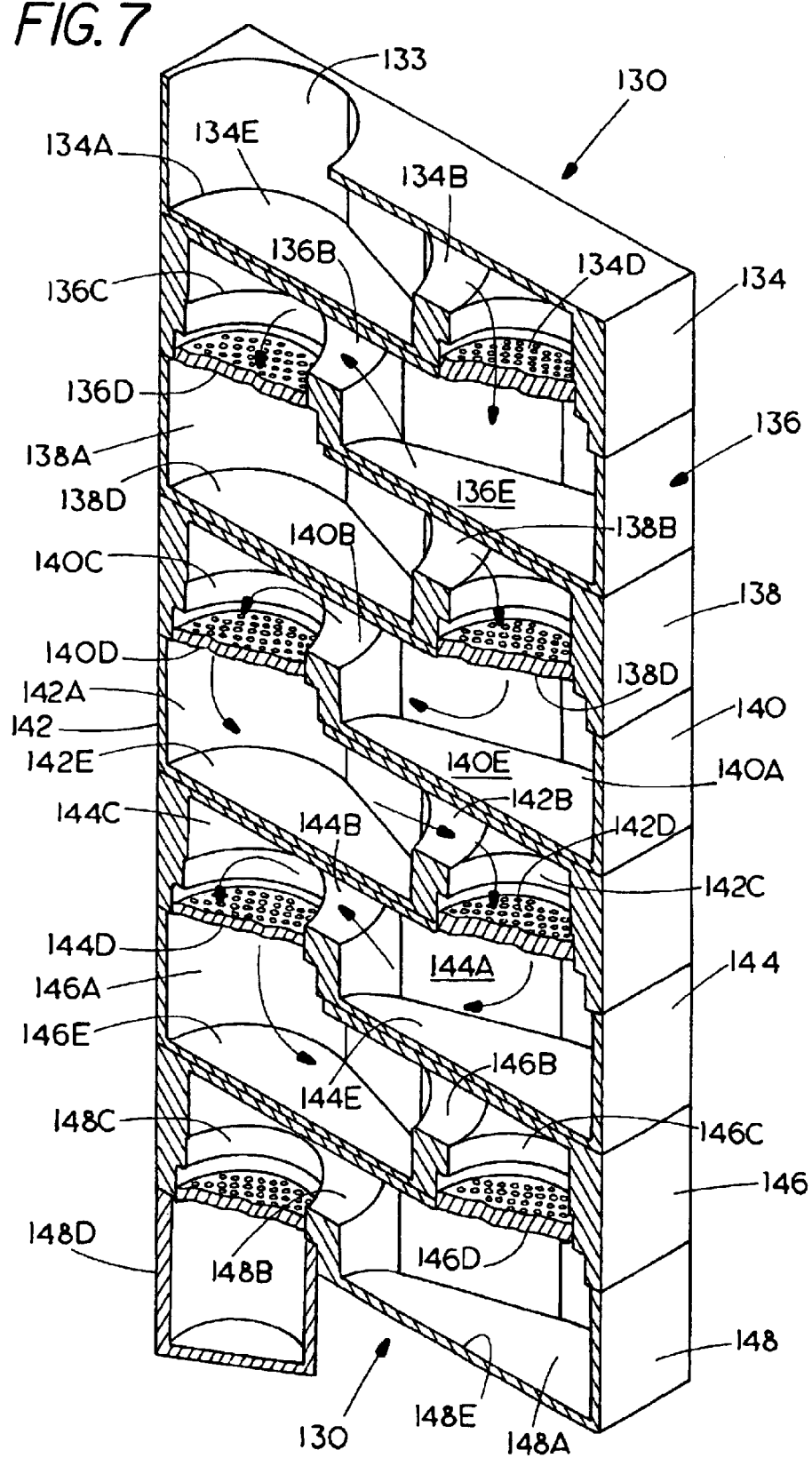
FIG. 7 is a perspective sectional view of a modified form of the invention.

In FIG. 7, a modified stacked cup design impactor embodying the principles of the present invention is illustrated at 130. The impactor 130 includes several individual stages. The impactor 130 has an inlet nozzle 133 that leads to a first impactor housing 134. The impactor housings are made essentially identical and vertically stacked so they can be separated. The direction of aerosol flow is reversed in the vertically adjacent impactor sections.

The first stage housing 134 has a tear drop shaped chamber 134A. The large end comprises an impaction surface 134E. The flow from the inlet goes through a cross or interstage passageway 134B and through a nozzle passage 134C that has a nozzle plate 134D therein. The nozzle plate 134D is for the second stage impactor and has large openings. The flow will then pass into a second stage impactor housing 136, which forms a chamber 136A and which has an impactor surface 136E. As indicated by the arrows, the flow goes through a passageway 136B to a nozzle passageway 136C and a third stage nozzle plate 136D, into a third stage impactor housing 138. A different size of openings in the nozzle plate 136D can be selected for a different cut point of particles.

A third stage chamber 138A has an impaction surface 138E, an interstage passage 138B, a nozzle passage 138C and a fourth stage outlet nozzle plate 138D.

A fourth stage housing 140, again has a tear drop shaped chamber 140A and particles from nozzle plate 138D impinge on fourth stage impactor surface 140E. The flow passes through a passage 140B, a nozzle passageway 140C and through a fifth stage nozzle plate 140D to a fifth stage housing 142, having a chamber 142A, and an impactor surface 142E. The flow goes through an interstage passage 142B and into a nozzle passage 142C and through a further small opening, sixth stage nozzle plate 142D to a sixth stage housing 144.

The sixth stage housing 144 has an impaction surface 144E, in the chamber 144A. The flow then goes through a passage 144B, and through a nozzle passage 144C and then through a seventh stage nozzle 144D into a chamber 146A of a seventh stage housing 146 with an impactor surface 146E. The flow will pass through a passage 146B, a nozzle passage 146C and a micro orifice filter 146D having openings thereon to achieve the desired filtering. The flow will impinge on an impactor plate in housing 148 which has a chamber 148A that receives the flow from the filter 146D. The flow then will pass out through an outlet opening 148C.

The stacked design of FIG. 7 uses the tear shaped chambers, as shown, for smooth flow, with little dead volume and thus little chance of having improper cut points. The housings can be separated for analysis of particles as will be shown.

Figure 8:
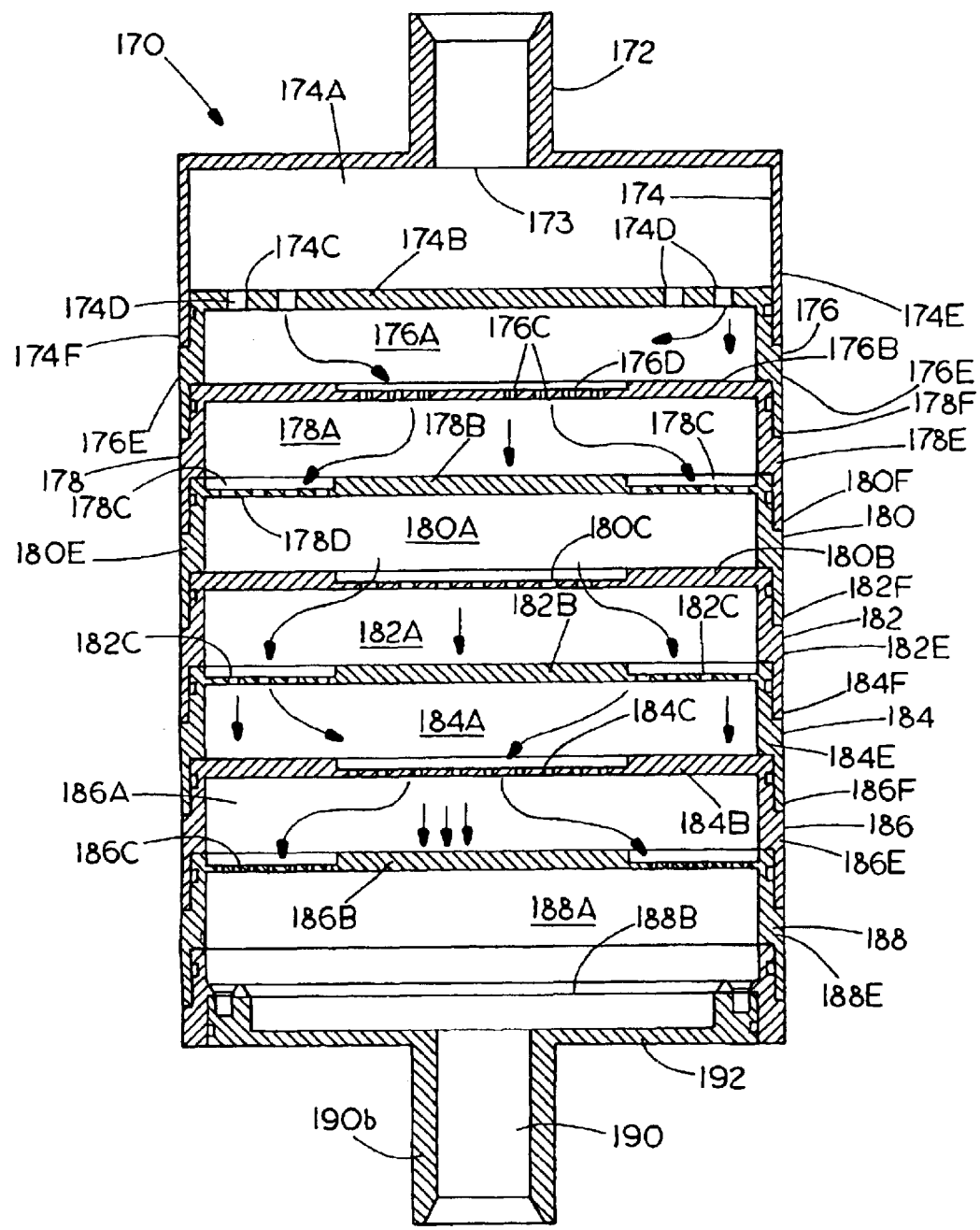
FIG. 8 is a vertical sectional view of a further modified form of the present invention.

A further modified form of an impactor is shown in FIG. 8. An impactor 170 is cylindrical and the impactor stage housing are removably mounted one above the other, as is common.

The impactor 170 has an inlet tube 172 that connects to a standard inlet as shown, and flow comes through the nozzle 173 into an inlet or first stage housing 174. Housing 174 has an impactor chamber 174A, with an impaction plate 174B aligned with the inlet nozzle 173. The impaction plate 174B is in the center portions of the chamber. The impaction plate portion 174B is surrounded by an integral annular nozzle ring 174C that has a plurality of orifices or openings 174D arranged around the periphery of the chamber 174A adjacent an exterior annular wall 174E. The flow will pass through the orifices or openings 174D into a second stage housing 176. The plate 174B and nozzle ring 174C from part of the top wall of the housing 176. The housing 176 has an outer annular wall 176E around plate 174B. Wall 176E has a shoulder 176F that receives an end of the housing wall 174E so the two housings removable nest together.

Housing 176 forms a chamber 176A into which the flow through the openings 174D passes. Particles above the cut off size impact on the surface of an annular impaction surface on wall plate wall 176B. The particles above the cut point will be collected on this annular surface 176B, and the flow in the chamber 176A inwardly toward the center of the chamber 176A and through a center nozzle section 176C in the center portions of the chamber, which has a pattern of openings or orifices 176D therein. The orifices 176D may be arranged in a square or circular pattern.

The flow through the nozzle openings 176D will enter into third, fourth, fifth, sixth and several impactor stage housings 178, 180, 182, 184, 186, and 188 in sequence, with the impactor plate positions alternating between the center and outer edge annular plate portions.

It should be noted that the walls forming the impaction surfaces are supported by the outer wall of the underlying housing. Each of the subsequent housings have chambers 178A, 180A, 182A, 184A, 186A and 188A respectively, with impaction surface 178B, 180B, 1828, 184B, 186B. A micro orifice filter 188B is in chamber 188A and leads to outlet 190. The nozzles are shown at 178C, 180C, 182C, 184C and 186C, respectively. The, housing walls 178E, 180E, 182E, 184E, and 186E have shoulders 178F, 180F, 182F, 184F and 186F, respectively, to support the housing above it. The outlet 190 is supported on a cover 192.

The impactor 170 provides the range of particle cut points as desired. The annular nozzles and center nozzles alternate between stages.

The impactor assembly 170 can be disassembled by pulling the telescoping or nesting parts of the housings apart.

Figure 9:
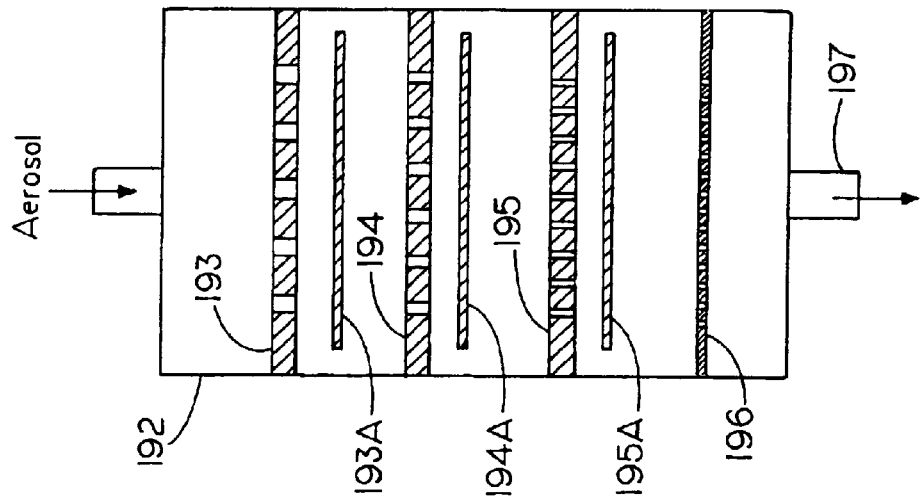
FIG. 9 is a schematic side sectional view of a typical cascade impactor with three impactor stages showing removable impaction plates, that can be slid in and out of the impactor.

FIG. 9 shows a general cascade impactor that will have a plurality of impaction plates that would be used in accordance with the processing sequence of the present invention.

A schematic representation is shown of an impactor, of general form which is indicated at 192. Stage 1 has a nozzle plate 193, with an impaction plate 193A held in place in a suitable manner. Stage 2, which is labeled, includes smaller orifices in nozzle plate 194 that provides impaction of particles onto an impaction surface of a plate 194A, and a third stage includes a nozzle plate 195 that has smaller nozzles which particles on an impaction plate 195A. A final filter 196 is illustrated, and an outlet 197 carries the flow out from the impactor assembly. Each of the impaction plates 193A, 194A and 195A and the final filter 196 can be individually removed, and are of a suitable size so that they will work for the processing according to the present invention illustrated in the following figures.

Figure 10:
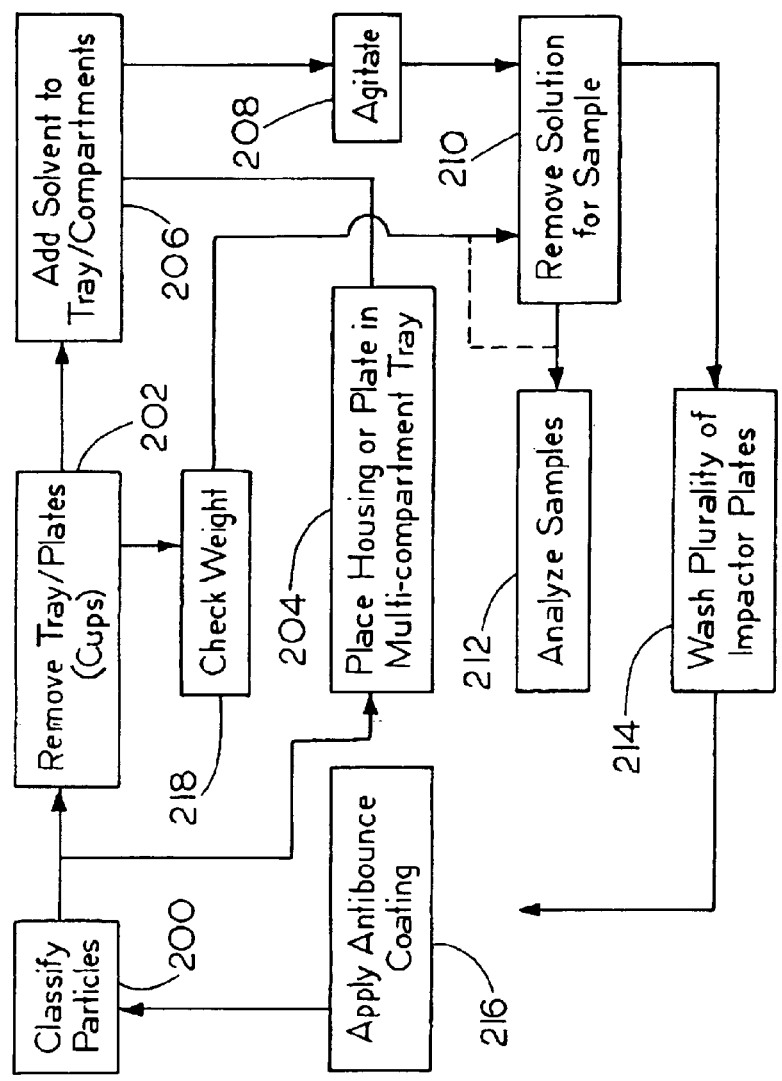
FIG. 10 is a block diagram of the analysis method of the present invention.

FIG. 10 is a flow chart that illustrates the process of the present invention for recovering samples, and performing other functions that are carried out. The invention relates to equipment that provides mechanically assisted operation, by recovering samples from a plurality of sample trays or impactor plates at a time, preferably using a tray of cups from the first form of the impactor, and a method of processing the samples more efficiently in a laboratory or industrial setting. The first step 200 is to classify particles in a typical impactor with a plurality of impactor plates. These can be the cups that are shown in the first form of the invention or individual plates in a multi-stage impactor that are illustrated in the previous figures. The cups or impactor plates will receive an anti-bounce coating, as represented at 216. The anti-bounce coating can be done right after washing the- impactor places, in a continuous process.

The particles are classified into individual impactor sections, whether it is in a tray of several cups as a unit, or individual impactor housing or impactor plates. The next stage is to remove a tray of a plurality of impactor cups such as that shown at 202 or, alternatively, if separable plates are used placing a plurality of plates, or individual housing sections into a multi-compartment container as indicated at 204. After either step the operator has a plurality of impactor plates having classified particles therein that can be handled as a unit.

The next step is to apply solvent to the plurality of impactor plates or compartments simultaneously as indicated at 206. This again is done with a plurality of samples, generally up to approximately eight samples.

Then, the plurality of plates (samples) are agitated as indicated at 208 with the solvent. This is done with a machine that agitates all of the multiple samples at once until the particles dissolve. Then the solution containing the components of interest is removed, as indicated at block 210, and the samples of interest are analyzed. This is indicated at 212. This is normally done in a high performance liquid chromatograph (HPLC).

Once the sample of the solution from each impactor plate is removed, the impactor plates or cups are washed, and this also can be done with a plurality of impactor plates at once. The impactor plates can be cups or housings, as well as flat plates. This is indicated at step 214 in FIG. 10. Anti-bounce coatings can be applied as indicated at box 216, and then the plates, cups or housings are ready for the next sequence of operations by putting them into a multi-stage or cascade impactor and classifying particles.

Various other alternatives and auxiliary operations can take place, such as weighing the individual impactor plates on electronic balances, as indicated at 218. This can take place after the trays have been removed, and then also after the samples have been removed at stage 210 to insure a known measure of liquid solvent. Volumetric measurement with a syringe is normally accurate enough.

FIG. 23 provides a detailed chart of various functions involved in this process for particle classification, particle dissolution, sample acquisition, washing and drying.

As shown in FIG. 11, the tray 36 from the first form of the invention can be lifted out of the impactor, leaving all of the individual impactor plates or cups in place. As shown, the cups 34, 46, 58, 66, 74, 82, 90, and 98. Thus, there are eight impactor plates formed by the cups that are lifted as one unit, after the impaction run has taken place, with all of the classified particles or aerosols carried in the cups. The cups are held in place in the trays by their respective flanges indicated at 34A, 46A, 58A, 66A, 74A, 82A, 90A, and 98A.

The tray 36 and cups are then moved as a unit to a dissolution station indicated at 224 in FIG. 12. The sectional view is taken on 12—12 in FIG. 11, so only four of the cups are shown. The basic form of the dissolution station includes a carrier or frame 226 that has centered support shafts 228 at opposite ends that are co-axial, and will permit rocking the carrier, tray 36 and cups about a generally horizontal axis. The shafts 228 can be supported on bearing posts 230, at least one of which has a removable top, to permit the carrier 226 to be inserted and removed from those posts when desired. The carrier 226 has a plurality of openings shown at 232, which are shaped, and oriented, to receive the egg or tear drop shaped cups carried by the tray 36, as shown in FIG. 11. The tray 36 then rests on the flat upper surface of the carrier or frame 226, with the impaction plates in the form of cups positioned in the openings 236. Then, a cover plate 238 is placed over the flanges 34A–98A of the respective cups, and clamped in place. Schematically shown is a stud 240 passing through an opening in the tray, and a wing nut on the stud 242 for clamping. It is to be understood that automatic or spring loaded clamps can be utilized. If desired suitable seals can be placed to seal along the cup flanges.

A reversible motor 244 drives the shaft. The motor is controlled by a controller 246, which can include a timer. The cover plate 238 has a series of small openings 247 therein, that align with the respective impactor plates formed as the cups 34–98, and a solvent is then introduced through these openings 247 with a suitable solvent dispenser, as shown schematically a syringe 248 or a manual pipette. The syringe 248 can be manually operated for quickly injecting a desired, measured amount of solvent into each of the impactor plate cups, or it can be automatically operated with a robot type, three axis dispensing transfer apparatus (see FIGS. 15 and 16).

Once the appropriate amount of solvent is in each of the plurality of impactor cups in this form of the disclosure, so the particles collected are immersed in the solvent, the motor 244 is started with the controller 246, and carrier 226 is then rocked back and forth about the axis of the shafts 228, generally as shown in FIG. 13 in dotted lines, from the solid line position. The cover plate 238 maintains the cups in position, and the solvent is then permitted to intermix adequately with the classified particles that are in the cups, until the desired component of interest has been dissolved.

Then, the motor 244 is stopped, and a clean syringe such as that shown at 248 is dipped into each of the individual cups through the openings 247 and a sample that is to be analyzed is withdrawn by suction from the syringe or a pipette. Typically 1 ml is withdrawn from each of the samples and put into an HPLC vial. This dispensing can also be done automatically with an automated handler as will be shown. The waste solution can be manually dumped, or the motor 244 driven to dump the waste solution automatically under control of controller 246, the waste also can be suctioned out with a manual pipette, syringe 248 or automatic syringe.

Figure 14:
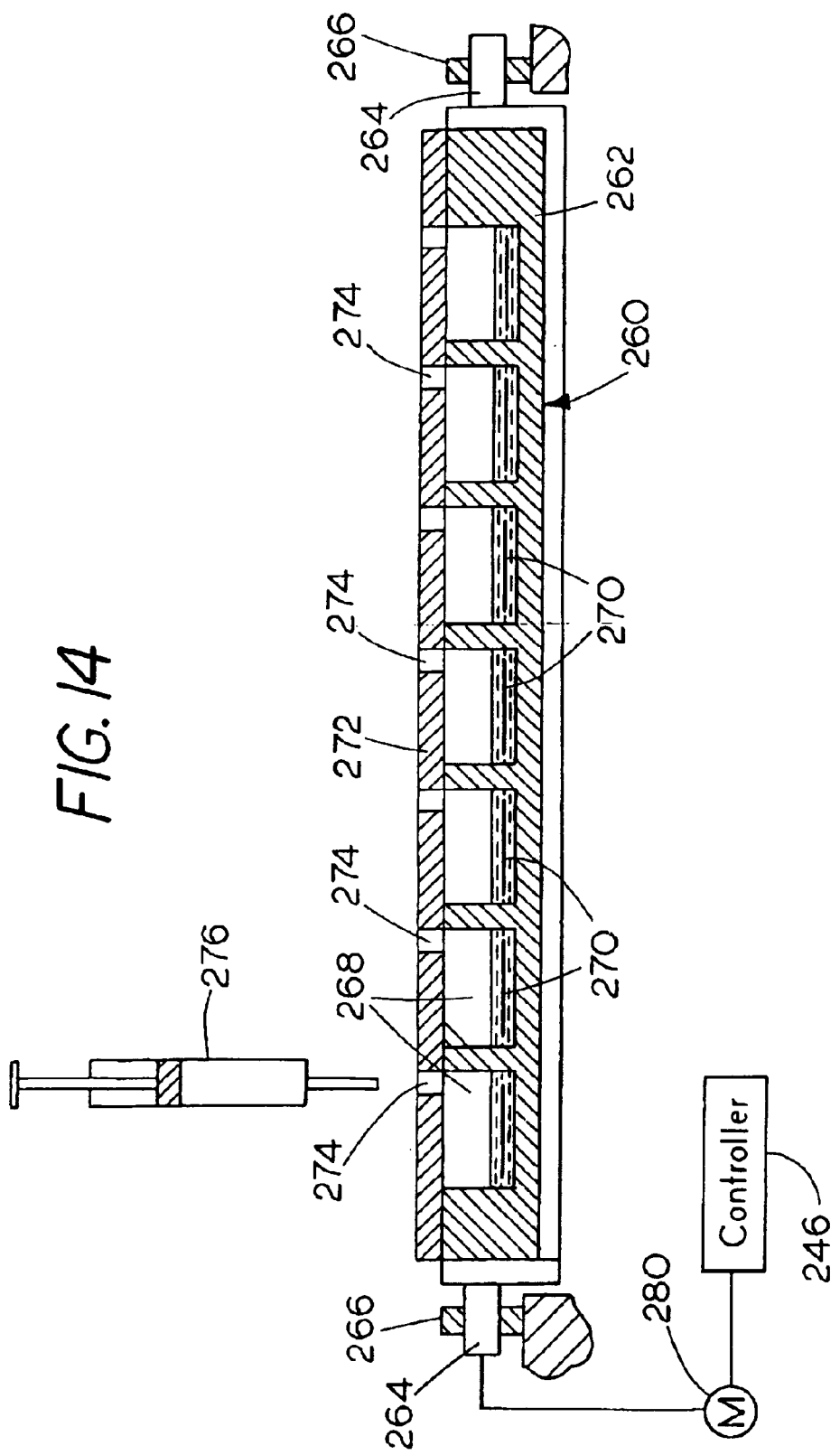
FIG. 14 is a schematic cross sectional view of a typical solvent holding tray in which separate substrates can be placed, such as those shown in the second, third, and fourth forms of the invention, for obtaining the samples in a solvent.

When an impactor plate that received classified particles is a flat plate, or as shown in the other forms of the impactors, is made up of individual housing segments that are stacked one on top of the other, and can be removed, a carrier that has closed bottom chambers of size to hold the individual impactor plates or the individual impactor housing sections may be used. As illustrated in FIG. 14, a multi-compartment carrier 260 is supported in a frame 262 that has shafts 264 thereon, that mount in bearing supports 266, as in the previous showing in FIG. 12. The carrier 260 has a plurality of chambers 268 formed therein, which have closed bottoms, and which are liquid tight. A plurality of individual impactor plates that are indicated at 270, one in each chamber. The flat plates are provided in many cascade impactors and shown in FIG. 9. The individual plates are put into the plurality of chambers 268.

If the individual vertically stacked impactor housing sections of FIGS. 7 or 8 are utilized, the chambers 268 can be made is suitable size and shape to receive the entire housing chamber, so that the particles in each interior chamber, which is open when the housing sections are separated, will be subjected to the solvent that is introduced.

In this form of the invention, a cover plate 272 is held over the chambers 268 in a suitable manner, such as with a stud, and wing nut as shown in FIG. 12, or with suitable latches. The cover plate 272 has a series of openings 274 that overlie and are aligned with the individual chambers 268, and into which a measured amount of a liquid solvent can be introduced using a syringe such as that shown in 276. The syringe can be manually or automatically operated and positioned so that the end of the syringe inserts through the openings 274 and injects the amount of solvent required into each of the chambers containing the substrate or impactor plate with the particles to be analyzed.

A variable speed motor 280, operated by the controller 246 can be energized, and the carrier can be rocked as shown in FIG. 13, for agitating the solvent and particles. In this case, the solvent is also indicated in the chambers 268. The impactor plates 270 are immersed in the liquid solvent and the rocking motion will cause the solvent to wash over the impactor surfaces and intermix with the particles for, dissolving the desired component from the particles on the impactor plates.

A sample of the solution containing the solvent and the dissolved component that has been dissolved will be removed from each chamber, and the samples will be transferred to vials for the appropriate analyzation instrument. This can also be done automatically using known robot type equipment.

Figure 15:
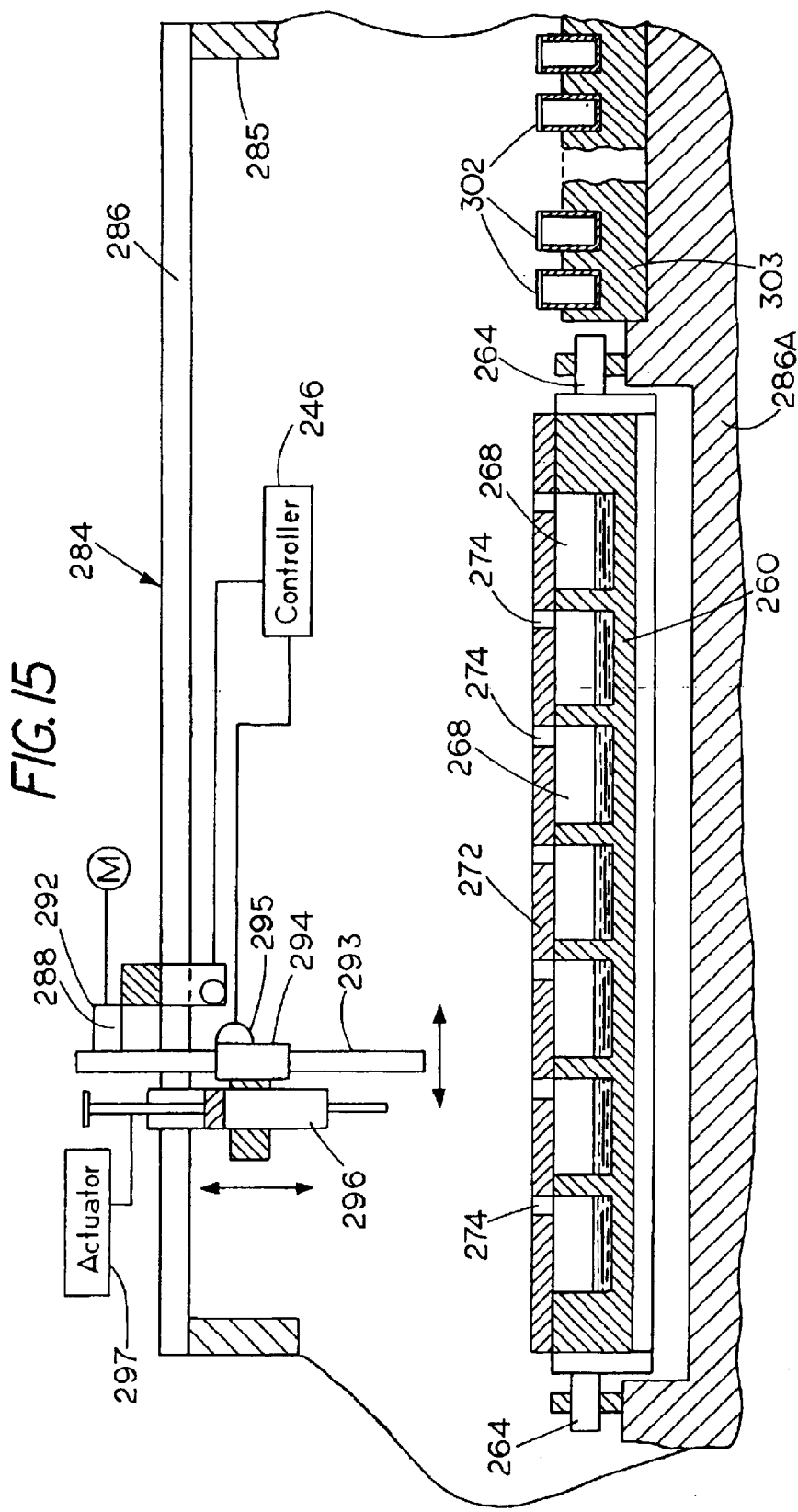
FIG. 15 is an exploded schematic view of a typical three axis holder for a syringe shown schematically adjacent a cross section of a sample recovery tray.
Figure 16:
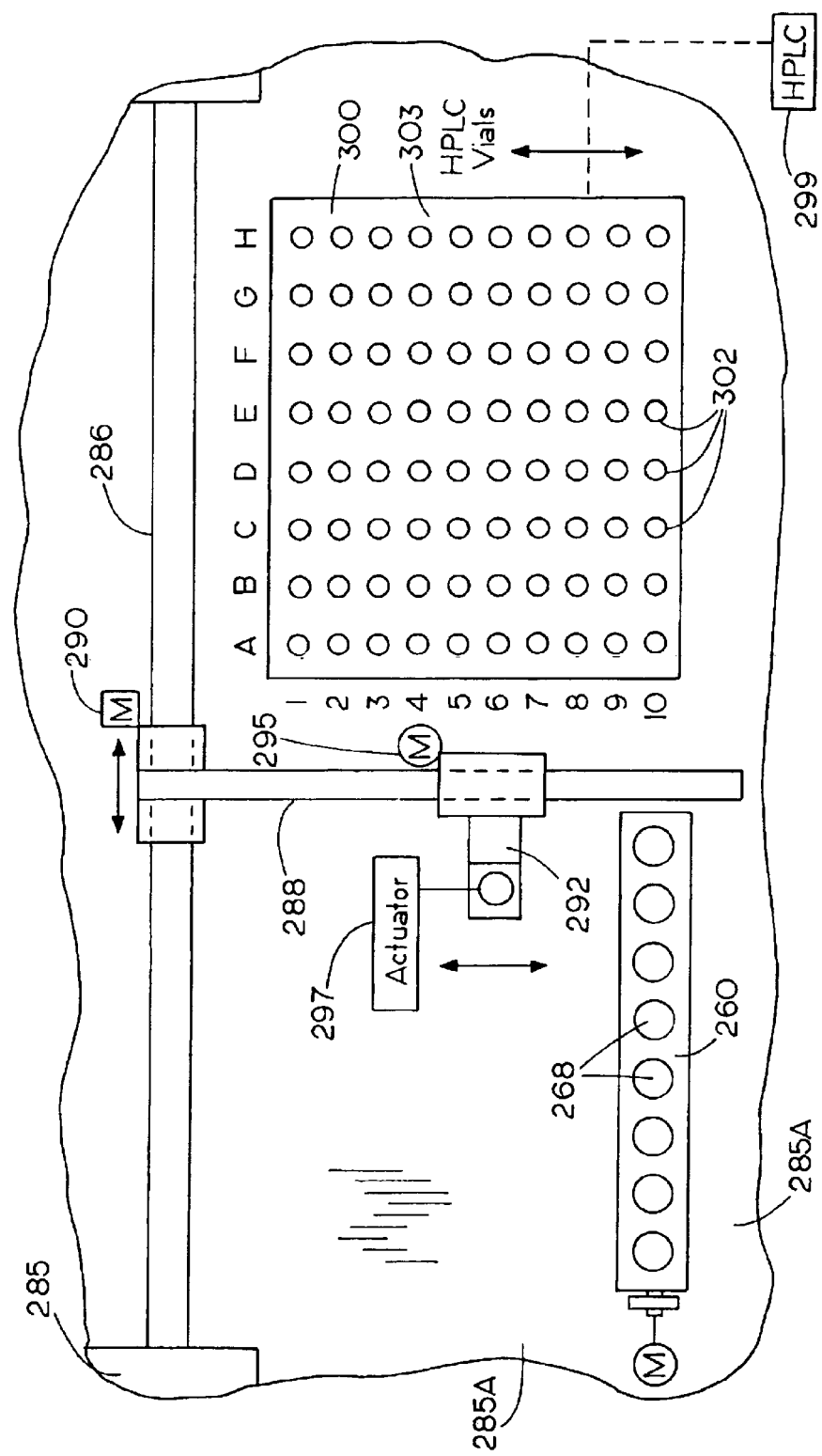
FIG. 16 is a plan view of the system shown in FIG. 9, illustrated schematically.

In FIGS. 15 and 16, a robot arm type liquid handler and injector is shown schematically. Such devices are available commercially, for example, Gilson, Inc., of Middleton, Wis. makes handler arms that will operate along three axes using a programmable controller for injecting one or several samples at the same time into one set of receptacles, and can be used for injecting solvents into the chambers used in the dissolution station, and then subsequent to the dissolving of the desired components, moving syringes into the chambers and extracting the solvent, as shown with the schematically illustrated syringes. The syringes are held in supports that are mounted on arms that will move to desired locations in X-Y coordinates in accordance with a computerized program and will lower the syringes along a Z axis into the chambers and then move to dispense the samples into vials held in a holder at a known position for analysis. Multiple probe handler model 215, made by Gilson, Inc., have the desired characteristics.

In FIGS. 15 and 16, a liquid dispenser and handler is illustrated generally at 284. While the frame is not shown in full, it is to be understood that the rail is supported by a frame 285 that couples to a table 285A forming part of the frame, and is operated through the controller 246, in a suitable manner. A fixed rail indicated at 286 extends transversely across the handler, and as shown in FIG. 16, the fixed rail has a laterally moveable arm 288 driveably mounted thereon using a suitable mounting hub and drive, again which is commercially available, operated by a motor 290, and controlled by controller 246.

The laterally moveable arm 288 is driven along rail 286 and in turn has a probe support block 292 thereon, which is driveably mounted on the moveable arm 288 for movement in a second axis along arm 288, perpendicular to the axis of the fixed rail 286. The block 292, in turn, mounts a vertically extending syringe probe 293, which has a sliding block 294 that can be driven up and down along the syringe probe 293, using a suitable motor 295, so that a syringe 296 supported on the block 294 can be moved vertically along probe or arm 293 to a position overlying one of the openings 274 in the cover plate 272 of the carrier 260 illustrated in place on table 285A in the dissolution station. The carrier 226 for the cups also could be mounted on the table. The syringe is operated with an actuator 297 under control of the controller 246.

FIG. 16 is a plan view of the handler, showing the carrier 260 in position but with the cover 272 removed. It has the chambers 268 for receiving circular impactor plates. The showing in FIG. 16 is schematic and not necessarily to scale. It can be seen that the carrier 260 (or 226) is supported on table 285A underlying the vertically extending probe 293. By properly programming the controls 246 the various drive motors will move the arm 288 along rail 286, the probe 293 along arm 288, and the syringe hub vertically along probe 293, when programmed with the location of the chambers 268 in carrier 260 and with the location of associated vials 302 in a rack or tray 300. The syringe 296 is moved as programmed. The syringe will be moved to positions overlying the openings 274 and initially inject solvent into the chambers 268 of the dissolution station carrier supported in place. After the rocking or mixing motion to dissolve the particles of interest, the syringe 296 can be relocated at a desired opening 274 and chamber 268, lowered and driven by actuator 297 to draw out a desired amount of the solution, which would include the dissolved particles or components of interest, and then moved to the tray support 300 that supports a number of individual HPLC sample vials 302 in desired coordinate positions that can be programmed into controller 246, and deposit the correct solution into a designated vial.

By using this type of a handler, the samples that are to be analyzed in an HPLC 299 can be quickly transferred to the vials and then the vials taken to a conventional chromatograph. More than one syringe 296 can be mounted on the vertically moveable block 290.

As an alternative to the use of a rocking carrier that will "slosh" the solvent across the impactor plates for aiding in dissolving the desired components from the particles, manual rocking and other agitation can be used. FIG. 17 shows an alternative form of agitation of a solution for dissolving the aerosol suitably. While a single dissolution chamber is shown in FIG. 17, it can be understood that the same type of carrier that would hold the tray 36 and the impactor cups, or a number of compartments for a plurality of sample substrates or impactor plates at one time would be used. In this form of the invention, a carrier 310 has chambers 312 formed therein, as shown, and is supported in a suitable manner relative to a framework. A cover 314 is used to enclose the chamber 312, and a suitable solvent indicated at 316 can be introduced in a suitable manner as described. The impactor plate or substrate 318 carrying the classified particles is shown in chamber 312. A piston and outer cylinder 320 have an outlet connected to a dip tube 322 that is in the individual chamber 312. Moving the piston up and down with a reciprocation drive, as shown by the block 324, so that the piston will move in opposite directions indicated by the arrow adjacent the drive block, will cause the fluid to move in and out of the dip tube 322. The movement of the piston causes liquid to be drawn into and expelled from the dip tube 322 to agitate the solvent 316 and accelerate the dissolution of the particles on the plate 318 in the solvent. An ultrasonic or mechanical vibration transducer shown at 326 also can be connected to the carrier 310 to provide ultrasonic vibration or energy or mechanical vibrator in the liquid solvent 316 to further enhance the dissolution process.

Following the dissolution of particles, the desired volume of the liquid sample can be transferred by an automatic or manual transfer syringe or pipette to a suitable vial, using the apparatus previously shown and explained or doing it manually.

In FIG. 17, a piston is shown a create a vacuum to draw liquid solvent up into the dip tube, and to provide a pressure to discharge the upwardly drawn liquid back into the chamber or cell 312, this can also be done by alternately connecting the dip tubes to a source of vacuum and a source of pressure through solenoid valves. For example, a rotary valve that alternately connects between pressure and vacuum can be driven, and the plurality of chambers or cells can be agitated as the valve is driven to alternate pressures in a dip tube.

FIG. 18 is a schematic representation of one way to measure the amount of solvent dispensed and recovered for record purposes. A quantity of solvent can be dispensed into a chamber of a separate calibration cell generally indicated at 328. Cell 328 is supported on an electronic balance 332 so that the amount of solvent indicated at 334 can be weighed. The solvent volume dispensed into the dissolution station can be checked by dispensing solvent into this cell 330, weighing it with the balance 332, when beginning a sample recovery cycle, placing the solvent into a chamber for dissolving particles, and at the end reweighing the solution, so that any change in volume in the cycle will be determined. An average value can be used.

The bases that are shown in FIGS. 12 and 14, for example, are made so that they will accommodate the cup tray, or impactor plates, and there is then a gentle rocker or optional mechanical or ultrasonic agitators can be used. The covers, with the holes in it allow the syringe to provide introduction of liquids, and removal of liquids. In operation, the user places the cup tray in the base and closes the lid, or places the impactor plates in the chambers and closes the lid. The liquid handler can then dispense the solvent into each cup, and this can be automatically done as shown. Dissolution takes place, either with the gentle rocker that is shown, the ultrasonic agitation, or mechanical agitation. The liquid handler, then as shown in the three axes arm, then removes the samples to HPLC vials. Optionally, the liquid handler can be programmed to come back and suck out waste solutions, with the rocker positioned so that base is slanted and the liquid will go over to one side of the cups or one side of the chambers. This can be combined with an automatic dish washer or clean up appliance.

In the semi automatic process the individual substrates or impactor plates can be coated with an "anti-bounce" or slightly resilient material, such as a silicone oil, as is well known. This is done before impaction, and in a continuous process would be done after the cups or impactor plates had been cleaned. FIG. 19 illustrates a coating station showing cups that are carried in the tray 36 in a housing for coating. The eight cups can be essentially coated with one manifold or housing that would overlie the cups held in the frame of individual impactor plates or impactor housing as shown in FIG. 7 are used, framed with chambers on which the dispensing manifold is mounted can be used.

The anti-bounce coating station apparatus 340 includes a support or frame 342 for supporting the impactor cups, or the tray 36 filled with cups A single cup shown at 344 is supported on its flanges on the cup tray 36 and then on the frame or the support 226, which can be mounted for rocking movement. A manifold body 346 is positioned over the cups, and can be clamped into place to the frame 226 in a desired manner as shown at 347. The coating manifold body 346 has openings 354 above each cup 344 for a pipette or syringe 384 to deposit solution directly into each cup 344. The dispenser 348 has an outlet tube that fits into the opening 354 and a piston 352 that moves up and down in the syringe barrel. A coating solution is introduced through the passageway 354. The coating material can be kept in a reservoir in the handle and introduced into the cups with valves that permit the liquid to flow into the cups.

The manifold body 346 has a gas or air duct 362 open to each cup. The duct 362 extends across all of the cups on each tray, and is connected to an air or gas source 364 through a suitable conduit and opening 360. The duct 362 is open to the cups 344, and an exhaust duct is provided on an opposite end of the manifold so the air or gas can be discharged. Each cup or chamber holding an impaction plate would have an individual passageway 354, but as shown all the cups are connected in parallel to the large gas or air duct 362.

The anti-bounce material introduced into the cups is known material, for example a mixture of silicone oil and hexane. The solution can be drawn into the dispenser 348 by raising the piston 352, and then upon reversal of the piston 352, the material will be discharged into the vertical passageway 354 and into the respective cup. Since the coating material is liquid it will flow across and cover the impaction surface of the cup. The support 226 is rocked as shown in FIG. 12 while the solvent in the coating mixture is vaporized and drying occurs. The air, which can include other gases, such as dry nitrogen, from the air source 364 will exhaust solvent (hexane) vapors from the coating material out through an air discharge opening like are inlet opening 360 at the other end of the manifold. The vapors can be routed to a hood or solvent recovery system. The openings 354 are small and do not discharge substantial amounts of vapor. Once the solvent is exhausted, there remains a uniform tacky coating of the appropriate thickness on the bottom surface of the cup or other impactor plate or substrate 344. By rocking the support, the impaction surfaces are all coated to a uniform thickness. The manifold can be sealed on the cup flanges with O-rings to avoid spillage.

Figure 21:
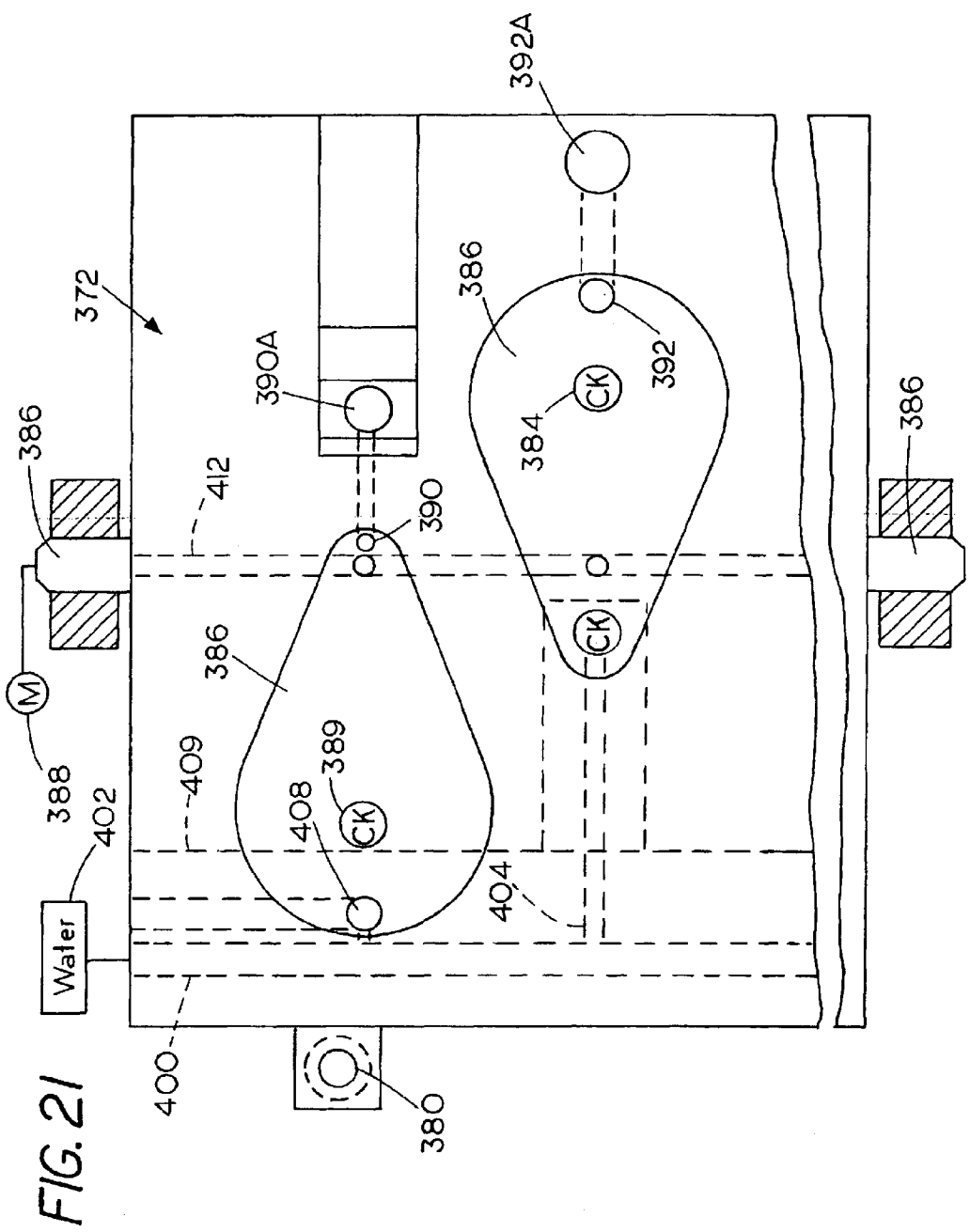
FIG. 21 is a sectional view taken on line 21—21 in FIGS. 20 and 22.

As part of the sample recovery and cleaning process, a combined station for sample acquisition, primarily, and alternately also for washing the impactor plates or trays, which are illustrated in FIG. 20. FIG. 21 is an inverted plan view taken on line 21—21 in FIG. 20 of the manifold plate of assembly that is used for particle dissolution, and sample acquisition and waste solvent disposal primarily, and with suitable correction for washing and rinsing substrates. In this form of the invention, a particle dissolution and sample acquisition/waste solvent disposal station is illustrated generally at 370, and it also can be used as a wash and rinsing station with appropriate manifold ducts. The assembly includes a manifold 372 that forms a cover over a base or substrate carrier 374. The base 374 has a series of openings therein indicated at 376, that are used for receiving the individual cups from the impactors shown in FIGS. 1–6. These cups are indicated by general number 378, in FIG. 20.

As can be seen, cup 378 has a flange 378A that is supported on the tray 36, from the first form of the invention, and eight of these cups then can be processed as a unit, after impaction, so each of the cups 378 includes particles as desired.

The manifold cover 372 then can be clamped in place with suitable schematically shown clamps 380, at desired intervals along the edges of the manifold and frame body 374 to hold the two parts together, and hold the flanges sealed. Suitable resilient seals typically shown at 371 are utilized. These seals can be pneumatic seals or soft O-rings that seal with low compression as shown previously.

If the station 370 is going to be used for dissolution of the particles for obtaining samples that are desired, a suitable solvent can be injected manually or automatically into each cup or compartment utilizing a syringe 382 through the individual openings 384 that lead into the recesses 386 forming chambers in the manifold over the individual cups 378. There would be eight of the openings, and each can have a check valve in them if desired, to prevent solution from sloshing back out the openings 384 as illustrated schematically. The check valves would permit liquid to be injected, but would prevent it from being expelled. A simple elastomeric flap valve can be utilized, that can be penetrated by the end of the syringe 371.

The frame or body 374 has shafts 386 at opposite ends thereof, as illustrated at FIG. 21, and a motor 388 can be used for reciprocating and driving the body 374, including the manifold cover about the axis of the shafts for agitation of the solution and dissolving of the components of interest that are in the cups 378.

Once the dissolving is done, and adequate dissolving of the solution has occurred, the motor 388 can be used for tilting the sample recovery station 370 approximately 45° in a clockwise direction shown in FIG. 20, as illustrated by the dotted lines, and a liquid solution that would include the solvent and other components of interest will drain from the cup 378 (there are eight of these cups) into a corner of the respective recess 386, through sample recovery passageways shown at 390 and 392. These passageways 390 and 392 open to vial holding openings 390A and 392A, which are of size to receive threads so that a neck of a sample recovery vial shown at 394 can be threaded into, or friction fitted into, the recesses 390A and 392A. The bores or openings 390A and 392A have vent tubes 396 held therein. The vent tubes 396 extend into the interior of the respective vial and permit air to vent out, so that when the body or frame 374 is brought back to its horizontal position, as shown in FIG. 20 in solid lines, the sample that had drained through the passageways 390 and 392 would be carried in the vials or bottles 394. In this position, and then after samples have been placed in the vials at a suitable amount of material for analysis, the vials can be manually removed, and taken to the analyzation station for analyzing the samples recovered.

The vials can have screw caps that are fiction fitted into the openings 390A and 392A, and in the other openings for the eight cups that are in assembly, so a robot arm could grip the vials and remove them from the opening. Adequate clearance would be provided relative to any supporting surface. The bearings for the shafts 398 would be on pedestals that would raise the frame 374 upwardly above the supporting surface sufficiently so that the tilting could occur, and that the vials could be removed easily.

After the samples have been decanted, the cups can be washed in place, in a number of different ways. As shown, the manifold cover 372 has an interior passageway shown at 400, that extends all the way along the length of the manifold cover 372. The passageway 400 would be connected with short passageways 404 to the recesses 386 so that a supply of water indicated at 402 could be provided to flush the underlying cups, sufficiently to provide cleaning. The cups could be drained into vials that were used for waste, or can be removed after being flushed with water and drained manually. However, putting in a limited amount of water into the cups and then rocking the cups back and forth if desired, drain passageways indicated at 408 can be provided over each one of the recesses 386. The passageways have check valves that would permit liquid to be exhausted outwardly, as indicated by the arrow into a duct 409, but prevent liquid from moving inwardly, so that by tilting the frame 374 counterclockwise to a position where it was substantially inverted, the chambers that were formed by the recesses 386 and the cups 378 can be permitted to drain. The duct 409 is connected to a suitable disposal hose or conduit and to drain.

Finally, if desired, drying air or hot nitrogen enriched air can be introduced through a conduit 412 that has branches leading to the individual cups, again with check valves that would prevent outflow from the cups, but would permit air to be blown into the individual cups. This passageway is a passageway that is connected in parallel to each of the recesses 386, and would cross the narrow ends of the recesses so that air could be blown in and then exhausted out through the waste passageways for air discharge. The duct 409 could discharge air to the drain to atmosphere, or to a filter for filtering the air being discharged.

In this way, a combined sample recovery station and wash station can be utilized for automating the process using the eight cups, or some other number of chambers in a suitable base such as that shown for the carrier 260, that would have a cover manifold similar to 372 mounted thereon.

The cups shown, and the impaction housing and individual plates, are impactor components that have impaction surface on which particles are collected. FIG. 22 shows a modified, manual dissolution and sample acquisition station.

In FIG. 22, the manifold shown in FIG. 20 is simplified, and provides the supports for the vials, and the recesses above the cups but not the ducts for water and air. The manifold can be clamped or held onto a body containing the individual cups, and then gently rocked, after manually adding solvent into the cups, for dissolution of the particles. Then the assembly is tilted for sample acquisition in each of the individual vials.

The manifold 370A includes the recesses 386, that mate with the base 374 and can be held in place on the base overlying the cups 378. The edges of the cups will be sealed with suitable seals. In this form of the invention, the cups can be filled manually with a suitable solvent before placing the manifold on the cups, or the manifold can have openings shown at 384A that will permit injection of material from a syringe 381 or pipette manually into each of the individual cups. The other portions of the manifold are as previously described, including the decanting passageways 390, 390A and 392 and 392A. The vials 394 can be put into position, and then the base 374 and the manifold 370A gently rocked manually until particles in the individual cups have been dissolved. The seals 371 will seal the cups to avoid spilling.

When the dissolution step is completed, by gently rocking the base and manifold 370A or if desired by vibrations and the like, the samples can be acquired by tilting the base and manifold to drain the solvent that has been introduced along with the dissolved particles through the passageways 390 and 392 into the respective vials 394, which then can be removed manually and sent for analysis.

This manual work station, thus is intended primarily for assisting an operator in performing the required manual steps. The waste/wash/dry functions can also be performed. The base 374 accommodates the cup tray and the cups 378, and as shown it can be rocked gently manually, or optionally with the mechanical or ultrasonic agitators that have been described. The manifold 370A has the decanting passageways and vial holding outlets, and the seals that will seal in the cup flanges to ensure the solvent will not leak.

In FIGS. 23 and 24, the support 226 supporting tray 36 and the cups forming impactor plates has a wash and dry manifold 400 supported over the top. The manifold can be Plexiglas and has a longitudinally extending passageway 402 connected to a water or solvent source 404. The passageway 402 is zigzagged so each opening 406 that opens to a respective cup overlies a portion of the cup. The passageway 402 discharges out the opposite end of the manifold from the connection to the source. A valve 408 can be used to restrict outflow so the amount of water discharged from opening 406 can be regulated.

A longitudinally zigzagged drying gas passageway 412 is also formed in the manifold 400 and it has a separate opening 414 over each cup. The passageway 412 is connected at one end to a dry gas source 416. When washing or rinsing the cups manually, water is introduced through passageway 402 and the manifold can be held in place and the cups agitated or rocked to wash the cups. The manifold can then be lifted and the cups drained. The manifold can be then placed over the cups again and a dry gas such as hot nitrogen enriched air or air is introduced through the passageway 412 for drying the cups. The cups are then ready to use again. No seals on the cups are needed for manual washing/rinsing, but can be used if desired.

As a summary of manual operation, the user places the cup tray 36 and the cups that are shown at 378 in the base and manually dispenses the solvent, such as with repeating pipettes or the syringe 381, and then the manifold 370A can be clamped in place or otherwise closed over the cups. Dissolution will take place either with the gently manually rocking, or with the motor driven rocker, the ultrasonic agitation, or some mechanical agitation. The user then can decant the samples into the vials manually, by tilting the base, and once the vials are removed, the user can attach liquid waste line fittings in place of each vial for draining the remaining solvent and then washing and flushing the cups and the rest of the passageways in the manifold. After waste is withdrawn, and rinse, wash, rinse, dry cycles can take place, as desired. Air can be introduced into the vial passageways by individual fittings or a manually placed air hose.

The connections can be made to a waste drain for tilting the manifold by tilting them into the bores where the vials are provided, and afterwards the washer rinse water can be introduced through the bores in a suitable manner.

In the form of FIGS. 23 and 24, the tray is covered with a manifold for introducing a solvent or water with detergent, rocking the trays, emptying them and then drying.

FIG. 25 is a summary chart showing various combinations of methods that can be utilized for carrying out the principles of the present invention. The methods of coating, which would be application of the anti-bounce coating, can be used in connection with any one of the methods of solvent addition, the methods of particle dissolution, the methods of sample acquisition, the methods of waste disposal, the methods of washing, or the methods of drying. Thus, there are large numbers of combinations that can be made.

By way of example, the anti-bounce coating can be done with manual pipetting, the solvent can be added with automatic pipetting, the dissolution can be done with gentle agitation, the sample acquisition can be done with an automatic syringe, the method of waste disposal can be done with automatic dumping, the method of washing can be manual, and the method of drying can be hot nitrogen enriched air. It can be seen that any one of the different selections can be used with any one of the other selections in each of the columns. It should be noted that the methods of dissolution include direct contact rubbing, which was not previously explained, that means that the solvent can be rubbed against the particles, and recirculation would include pumping the material or moving the material a number of times against the particles for dissolution.

In the method of sample acquisition, the decanting step is that illustrated with the apparatus of FIGS. 20, 21 and 22. Waste disposal by suction is merely drawing the waste solutions with a vacuum, or with a syringe that sucks the material out. The other steps are self-evident, it is believed.

Manual operations of the described work station in FIGS. 12–14 uses the components for assisting an operator in the required manual steps. FIGS. 22, 23 and 24 are also designed as a manual station. The dissolution, sample acquisition, and waste/wash/dry functions are combined in the devices of each of FIGS. 12 and 14 into one unit. The base that accommodates cup tray or the impactor plates can be manually rocked, or the motor for the gentle rocker or optional mechanical or ultrasonic agitators used. The cover has decanting passageways and vial ports, as shown in FIG. 22 and also accomplishes an O-ring seal. The user places the cup tray in the base (FIG. 12) or places the impactor plates in compartments (FIG. 14), and manually dispenses solvent (likely with a repeating pipette). The cover or lid can be put on if not done earlier. Dissolution takes place, either with manual rocking, the motorized gentle rocker, ultrasonic agitation, or mechanical agitation. User then decants or removes and places the samples into vials.

In connection with FIG. 22, once vials are removed, the user attaches liquid waste line fittings in place of each vial and can tilt the unit to dump waste, then the rinse, wash, rinse, dry cycle can be carried out as desired.

For dissolution of the particles, the supports for the cup or impactor plates or tray can be rocked slowly back and forth, about 5 to 20 degrees, particularly in relation to FIGS. 12 and 14. The covers will prevent contamination and eliminate any meaningful solvent loss; the cover does not need to accomplish a liquid seal, and the cover may have holes in it to allow addition and removal of solvent. The particles can be manually rubbed by direct contact using a pad on a handle.

The Ultrasonic Dissolver may be made to accommodate cup tray and cups or a base with connections. The base can have electronic connection so when the cover closes electrical contact is made. In this case the cover also accomplishes a pneumatic seal to avoid splashing and contamination of neighboring cups.

The Mechanical Dissolver accommodates the cup tray and the base has mechanical agitators, such as vibrators. Here too, the lid can be used to start the agitation and to accomplish a seal to avoid splashing and contamination of neighboring cups.

Washing can also be done by placing the cups in a kitchen dishwasher using dish detergent.

Although the present invention has been described with reference to preferred embodiments, workers skilled in the art will recognize that changes may be made in form and detail without departing from the spirit and scope of the invention.

What is claimed is:

1. A process for obtaining samples for analysis from a cascade impactor comprising providing a plurality of impactor components having impaction surfaces carrying particles that have been classified, supporting the plurality of impactor components on a support, such that the impactor surfaces of the plurality of impactor components are separated and enclosed to form separate enclosures, injecting a solvent solution into each of the plurality of enclosures containing an impaction surface, agitating the solvent applied on each separated and enclosed surface by moving the support so that the plurality of the separated impaction surfaces are agitated simultaneously, and removing a desired amount of liquid for a sample from each separate enclosure.

2. The method of claim 1, including transferring the samples to vials, for an instrument used to analyze the samples.

3. The method of claim 1, including agitating the solvent in all of the separate enclosures by rocking the support for the plurality of impactor components.

4. The method of claim 1, including agitating the solvent in all of the separate enclosures by rocking the support for the plurality of impactor components.

5. A method of obtaining samples from a plurality of separated impaction surfaces on which classified particles have been deposited, comprising supporting a plurality of the impaction surfaces, each in a separate enclosed chamber on a common carrier, introducing a solvent into each of the enclosed chambers, agitating the solvent in all of the enclosed chambers simultaneously to dissolve particles on the impaction surfaces, and providing separate fluid connections to each of the enclosed chambers for the impaction surfaces for the introduction of the solvent.

6. The method of claim 5, including removing a sample from each of the chambers held on the carrier.

7. The method of claim 6, and washing the plurality of chambers simultaneously while supported on a carrier.

8. The method of claim 5, wherein each of said chambers is formed by a cup having flanges around the edges thereof, the impaction surfaces being on the interior of the cup, supporting the flanges on the carrier and providing a manifold overlying the plurality of cups on the carrier, and the step of providing fluid connections comprising providing separate openings in said manifold to access each cup separately for introducing solvent and removing samples from the respective cup.

9. The method of claim 8, including sealing the periphery of each cup relative to the manifold.

10. The method of claim 8, including utilizing a syringe for introducing solvent into each of the chambers and removing samples subsequent to dissolution of particles in the solvent.

11. A method of processing particles held on impactor plates in separated chambers comprising selecting one of the methods of adding solvents to each chamber consisting of manual pipetting and automatic pipetting; selecting one of the methods of dissolution of particles in the solvent comprising using one of the group consisting of gentle agitation, mechanical vibration, ultrasonic vibration, recirculation, and direct contact rubbing; acquiring a sample from each chamber after the dissolution step by one of the methods of sample acquisition consisting of a manual syringe, an automatic syringe, or decanting liquid from the cup from the dissolved sample; and thereafter disposing of waste sample solutions in each chamber and, washing and drying the impactor plates.

12. The method of claim 11, including further coating the impactor plates with an anti-bounce coating by one of methods in the group consisting of manual pipetting, and automatic pipetting, followed by drying with a gaseous fluid.

13. The method of claim 11, wherein waste disposal is accomplished by one of the group consisting of manually dumping, automatically dumping, or sucking material from a chamber containing an impactor plate.

14. The method of claim 11, wherein said washing is accomplished by one of the group consisting of manual washing, or utilizing a special wash station having passageways for introducing liquid and discharging liquid, and passageways for air drying.

15. The method of claim 11, wherein drying comprising one of the group consisting of manual drying, hot air drying, and hot nitrogen enriched air drying.

* * * * *

UNITED STATES PATENT AND TRADEMARK OFFICE
CERTIFICATE OF CORRECTION

PATENT NO. : 6,723,568 B1
DATED : April 20, 2004
INVENTOR(S) : Liu et al.

It is certified that error appears in the above-identified patent and that said Letters Patent is hereby corrected as shown below:

Column 19,
Lines 60-62, please cancel Claim 4, and substitute the following:
-- 4. The method of claim 3, including washing the plurality of impaction surfaces simultaneously in a support. --

Signed and Sealed this

Thirtieth Day of November, 2004

JON W. DUDAS
*Director of the United States Patent and Trademark Office*

UNITED STATES PATENT AND TRADEMARK OFFICE
Certificate

Patent No. 6,723,568 B1                                          Patented: April 20, 2004

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Benjamin Y. H. Liu, North Oaks, MN (US); Virgil A. Marple, Maple Plain, MN (US); Daryl L. Roberts, Blaine, MN (US); and Nicholas C. Miller, White Bear Lake, MN (US).

Signed and Sealed this Third Day of July 2007.

JILL A. WARDEN
*Supervisory Patent Examiner*
Art Unit 1743